United States Patent
Mitelberg et al.

(10) Patent No.: US 11,864,751 B2
(45) Date of Patent: Jan. 9, 2024

(54) ENDOSCOPIC TISSUE APPROXIMATION SYSTEM AND METHODS

(71) Applicant: BOSTON SCIENTIFIC SCIMED, INC., Maple Grove, MN (US)

(72) Inventors: Vladimir Mitelberg, Austin, TX (US); Thomas Neudeck, Austin, TX (US); Ryan Gilkey, Kyle, TX (US); Naser Ahmad, Liberty Hill, TX (US); Andrew Gant, Austin, TX (US); Donald K. Jones, Dripping Springs, TX (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 323 days.

(21) Appl. No.: 16/701,276

(22) Filed: Dec. 3, 2019

(65) Prior Publication Data

US 2020/0178956 A1 Jun. 11, 2020

Related U.S. Application Data

(60) Provisional application No. 62/928,516, filed on Oct. 31, 2019, provisional application No. 62/775,542, filed on Dec. 5, 2018.

(51) Int. Cl.
*A61B 17/04* (2006.01)
*A61B 17/00* (2006.01)

(52) U.S. Cl.
CPC ...... *A61B 17/0469* (2013.01); *A61B 17/0401* (2013.01); *A61B 2017/00004* (2013.01);
(Continued)

(58) Field of Classification Search
CPC ............ A61B 17/0469; A61B 17/0401; A61B 2017/00004; A61B 2017/0437;
(Continued)

(56) References Cited

U.S. PATENT DOCUMENTS

| | | | |
|---|---|---|---|
| 8,287,556 | B2 | 10/2012 | Gilkey et al. |
| 8,540,735 | B2 | 9/2013 | Mitelberg et al. |

(Continued)

FOREIGN PATENT DOCUMENTS

| | | |
|---|---|---|
| JP | 2017536172 A | 12/2017 |
| WO | 2016087934 A1 | 6/2016 |
| WO | 2020117920 A1 | 6/2020 |

OTHER PUBLICATIONS

International Search Report and Written Opinion dated Apr. 1, 2020 for International Application No. PCT/US19/64441.

*Primary Examiner* — Julian W Woo
(74) *Attorney, Agent, or Firm* — Seager, Tufte & Wickhem, LLP

(57) ABSTRACT

A deployment system includes a sheath, a torque able shaft having a handle positioned at its proximal end, a detachable helical first suture anchor positioned at the shafts distal end and an elongate suture fixedly coupled to the suture anchor. The deployment system can be positioned at a first tissue, and the shaft rotated to advance the helical first suture anchor into engagement with the first tissue. The shaft is detached from the first suture anchor thereby deploying it at the first tissue location. Then, the deployment system is removed from the patient, and a second suture anchor is coupled to the distal end of the shaft. The deployment system is re-inserted into the patient and the distal end of the system is moved adjacent a second tissue location, and the process is repeated for a second suture anchor at the second tissue location. A suture extends between the first and second fasteners, and tension is applied to the suture to draw the first and second tissues toward each other to reconfigure the tissue.

40 Claims, 17 Drawing Sheets

(52) U.S. Cl.
CPC .......... *A61B 2017/0437* (2013.01); *A61B 2017/0441* (2013.01); *A61B 2017/0443* (2013.01)

(58) Field of Classification Search
CPC .... A61B 2017/0441; A61B 2017/0443; A61B 2017/00296; A61B 2017/0409; A61B 17/00234
See application file for complete search history.

(56) References Cited

U.S. PATENT DOCUMENTS

| | | | |
|---|---|---|---|
| 9,107,654 | B2 * | 8/2015 | Chang ............... A61B 17/0401 |
| 9,788,831 | B2 | 10/2017 | Mitelberg |
| 10,238,411 | B2 | 3/2019 | Mitelberg et al. |
| 11,446,023 | B2 * | 9/2022 | Binmoeller ...... A61B 17/07207 |
| 2001/0046518 | A1 | 11/2001 | Sawney |
| 2002/0077631 | A1 | 6/2002 | Lubbers et al. |
| 2004/0267317 | A1 | 12/2004 | Higgins et al. |
| 2007/0049942 | A1 | 3/2007 | Hindrichs et al. |
| 2007/0276408 | A1 | 11/2007 | Filipi et al. |
| 2008/0306511 | A1 | 12/2008 | Cooper et al. |
| 2009/0125039 | A1 | 5/2009 | Mikkaichi et al. |
| 2009/0276038 | A1 | 11/2009 | Tremulis et al. |
| 2010/0106166 | A1 | 4/2010 | Cropper et al. |
| 2011/0166649 | A1 | 7/2011 | Gross et al. |
| 2011/0301698 | A1 | 12/2011 | Miller et al. |
| 2013/0226233 | A1 | 8/2013 | D'Agostino et al. |
| 2014/0088644 | A1 | 3/2014 | Flint |
| 2014/0275756 | A1 | 9/2014 | Bender et al. |
| 2017/0000609 | A1 | 1/2017 | Gross et al. |
| 2017/0056228 | A1 | 3/2017 | Saadat et al. |
| 2017/0086818 | A1 | 3/2017 | Mitelberg |
| 2017/0156719 | A1 | 6/2017 | Tobis |
| 2018/0028180 | A1 | 2/2018 | Binmoeller et al. |
| 2018/0199937 | A1 | 7/2018 | Nesher et al. |

* cited by examiner

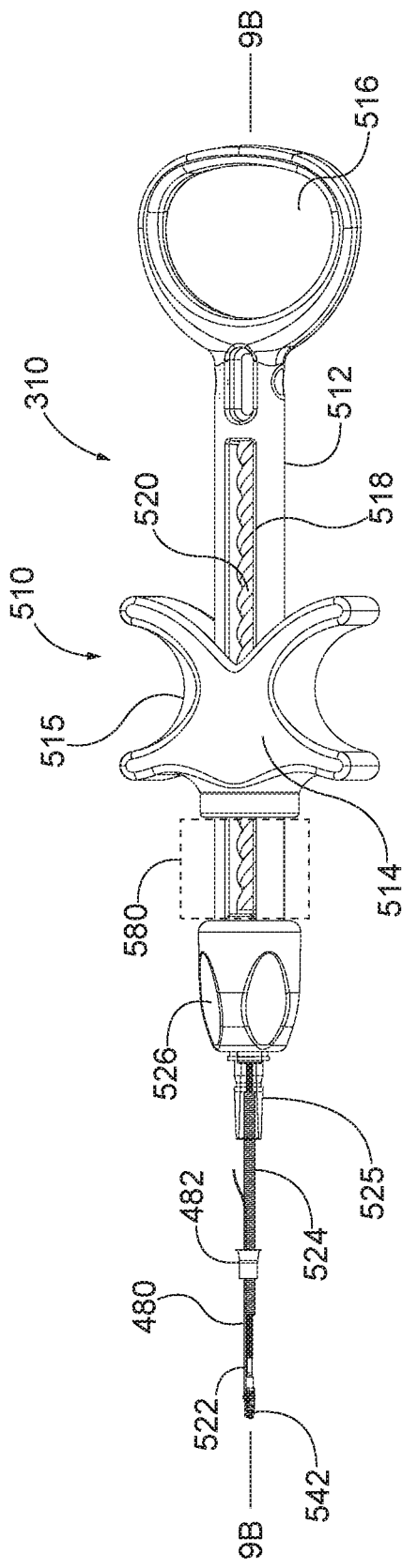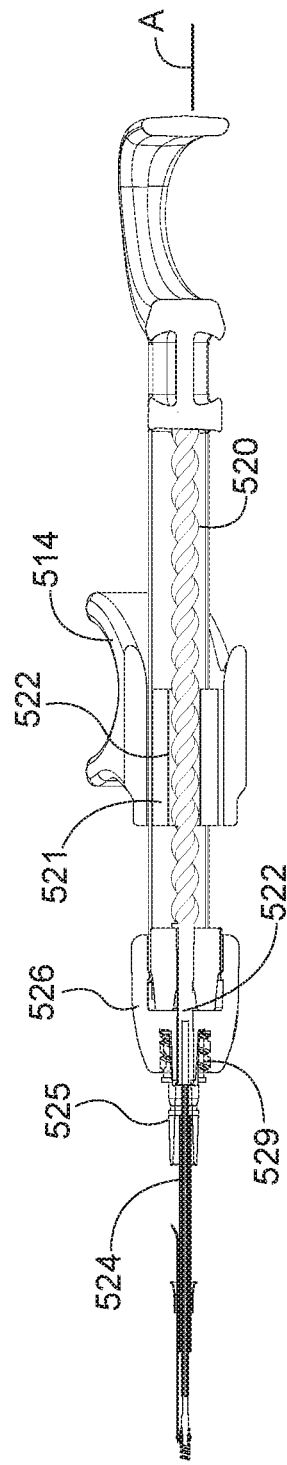
FIG. 9A
FIG. 9B

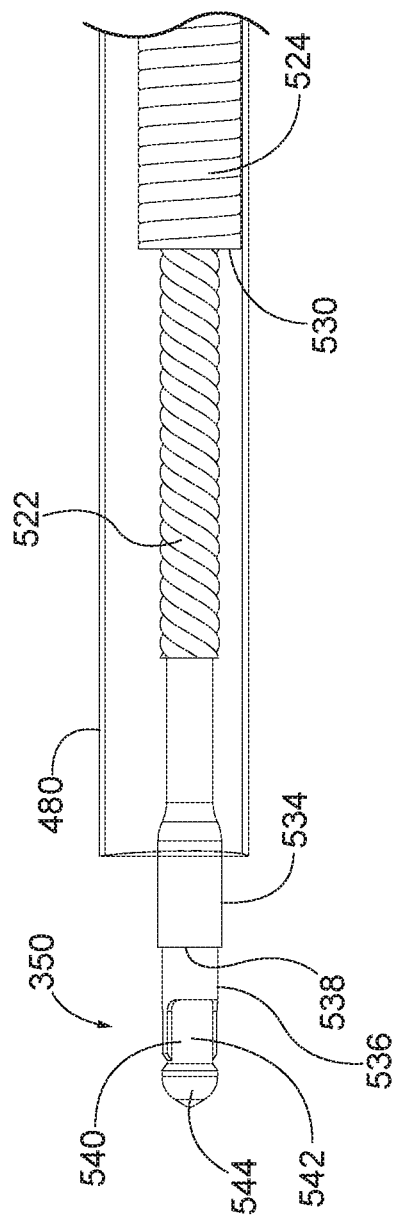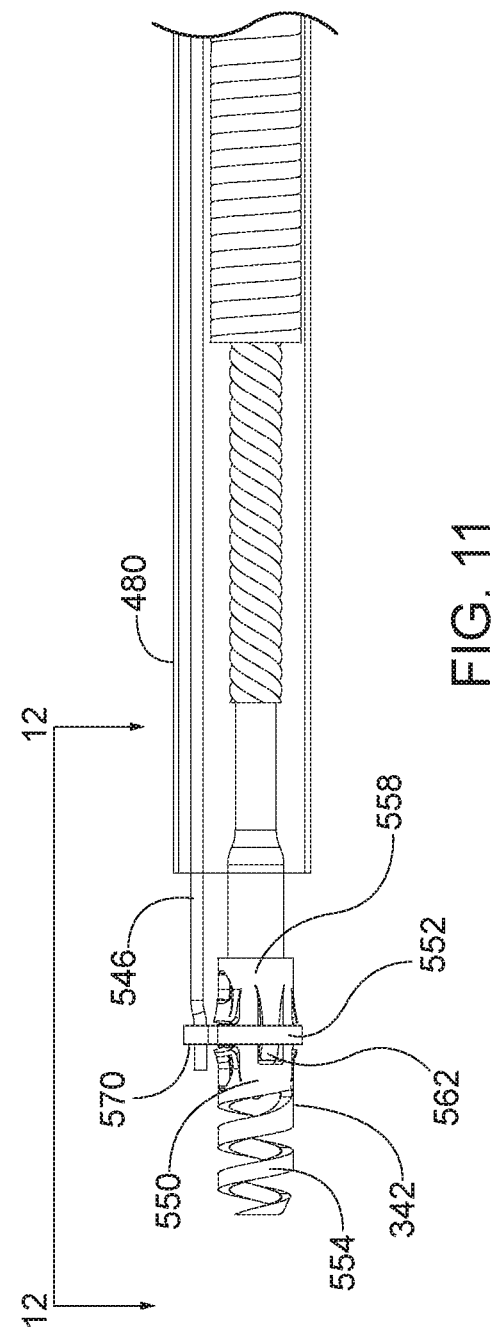

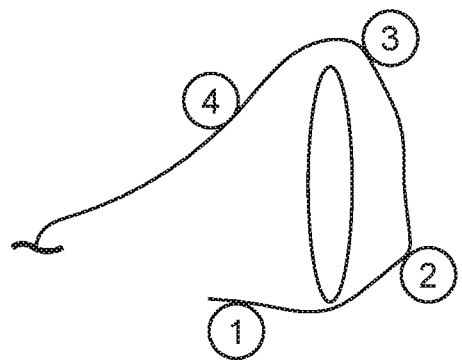
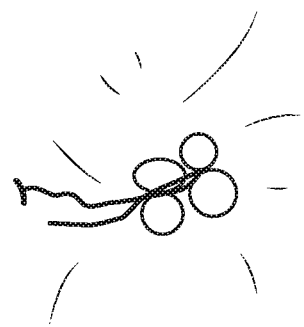
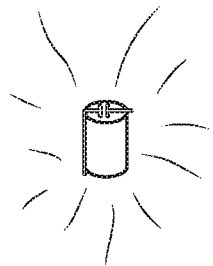
FIG. 25　　　　FIG. 26　　　　FIG. 27
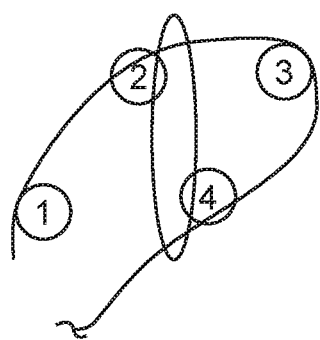
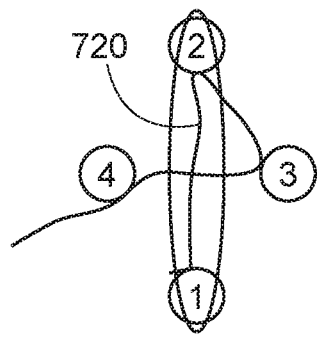
FIG. 28　　　　FIG. 29

ENDOSCOPIC TISSUE APPROXIMATION SYSTEM AND METHODS

CROSS REFERENCE TO RELATED APPLICATIONS

This application claims priority from U.S. Provisional Ser. No. 62/928,516, filed Oct. 31, 2019 and U.S. Provisional Ser. No. 62/775,542, filed Dec. 5, 2018, all of which are hereby incorporated by reference herein in their entireties.

BACKGROUND

1. Field of the Invention

The present disclosure relates to surgical instruments and methods. More particularly, the disclosure relates to instruments for deploying fasteners, hemostatic clips, as well as suturing methods and devices for use in endoscopic, laparoscopic, and other surgically open or minimally-invasive procedures.

2. State of the Art

Numerous conditions occur in the gastrointestinal tract requiring intervention including Gastrointestinal ("GI") bleeding and perforations. GI bleeding is often associated with peptic ulcer disease and if left untreated can be fatal. When a suspected GI bleed occurs in a patient, the Endoscopist can perform a diagnostic endoscopy to identify the lesion and determine the best course of treatment. From an endoscopic standpoint, the Endoscopist has a few options available in which to treat the patient. If the bleed is small the Endoscopist may be able to utilize thermal cautery to cauterize the lesion and obtain hemostasis. The thermal cautery treatment is typically used for well identified focal lesions and carries a risk of causing a perforation with the cautery probe. Re-bleeds are a common outcome of this therapy.

An alternative method to achieve hemostasis involves the use of endoscopically placed hemostasis clips. When properly placed, the hemostasis clips provide a compressive force at the site of the bleed to cause hemostasis. While the clips are easy to use, they are difficult to precisely position with respect to a lesion and once "fired" they lack the ability to be removed and repositioned. This often leads to multiple clips being used to control a bleed or to close a perforation. In addition, each clip is small and has the surface area to act only on a localized area of tissue Another method to control GI bleeding endoscopically is to use a suturing device like the system disclosed in U.S. Pat. No. 8,287,556 to Gilkey et al. The suturing device is coupled to a dual channel endoscope and is capable of interrupted or continuous stitching. The site of the bleed can be sutured and cinched to provide hemostasis. Additionally, if the bleed was accompanied with a perforation, the suturing device could be used to stitch the perforation closed. While capable of controlling a GI bleed, this suturing system is fairly complex and must be used with a specialized two channel therapeutic endoscope which is not widely available. There exists a need for a less complex solution for the treatment GI bleeds and perforations.

Other GI procedures that include creating anastomoses, closing perforations in the GI tract and tissue reconfiguring procedures for treating ulcers, require the ability to accurately and selectively target the intended tissue for reconfiguring or approximating while excluding non-targeted tissues and organs. These requirements also hamper other endoscopic procedures involving the stomach and other organs. For example, a number of open surgical procedures have been developed for controlling gastroesophageal reflux disease. Illustratively, in one such procedure, rings are created about the proximal stomach that act as a barrier to the unraveling of the lower esophageal sphincter. However, when these procedures are carried out endoscopically, limitations in endoscopic suturing techniques make the procedures difficult.

One solution has been proposed in US2007/0276408 to Filipi et al., wherein an instrument is described that is removably or permanently attached to the end of an endoscope or integrally fabricated with the endoscope. The described instrument includes a belt with a number of slots that carry a plurality of T-fasteners in a side-by-side circumferential arrangement. The T-fasteners are connected to each other by a continuous suture. The belt can be rotated about the end of the endoscope so that the slots, and consequently the T-fasteners, are moved into alignment with a push rod positioned within a working channel of the endoscope. Operation of the push rod can advance an aligned T-fastener out of the belt and into tissue, while the deployed T-fastener remains coupled to the suture. After each deployment of a T-fastener, the belt is rotated to displace an adjacent T-fastener into alignment with the push rod, and the push rod is again operated to deploy a subsequent T-fastener. The process is repeated to deploy additional T-fasteners. After the T-fasteners are deployed into the tissue, the suture can be tensioned to draw the fastened tissue into apposition and then cinched relative to the tissue to maintain the tension to permanently reduce the space between the fasteners. Thus, in one procedure, the volume of the stomach can be reduced to treat obesity or, in another procedure, the lower esophageal sphincter can be reinforced to reduce gastroesophageal reflux.

However, the Filipi et al. system has several disadvantages that render its use impractical. First, in various embodiments, the system may require modification of a standard endoscope, either by permanent attachment thereto or integral fabrication of the system at the distal end thereof. However, surgeons are known to prefer to use the endoscopes with which they are familiar, and would not readily permanently modify a very costly endoscope for a limited use purpose. Second, the system in all embodiments has a diameter larger than the end face of the standard endoscope. This results in a bulky instrument that is less maneuverable and somewhat unwieldy when operating in tight spaces or small body cavities. Third, the system requires that the belt and all fasteners on board be driven in a rotational movement at the distal end of the endoscope so that the belt and each subsequent T-fastener can be advanced into alignment with the push rod for T-fastener deployment. Such mechanical movement is difficult to effect at the distal end of the endoscope. Any misalignment would result in a failure to deploy a T-fastener or misfire of T-fastener. Fourth, the T-fasteners are deployed without knowledge of what tissue lies behind the target tissue. Therefore, it is possible for a deployed T-fastener to pierce unintended tissue behind the target tissue and cause damage. Fifth, it appears that the system, in practicality, requires deployment of all T-fasteners loaded into the slots of the belt before the endoscope may be withdrawn from over suture for securing the suture with a cinch. Therefore, the system is not particularly suited to flexible surgical procedure. For these and other reasons, a need remains for new devices and methods.

SUMMARY

A suture anchor, an arrangement of a plurality of suture anchors, a deployment system for deploying one or more suture anchors along with suture into tissue, and methods are provided herein.

The suture anchor is a type of fastener that includes a helical portion that is adapted to engage tissue and be retained in said tissue. The suture anchor includes a distal helical portion and a proximal receptacle portion. The suture anchor has a longitudinal axis that extends through the receptacle and helical portions. A suture eyelet is fixedly coupled to the suture anchor between the proximal and distal portions and is rotatable about the longitudinal axis of the suture anchor. The suture anchor receptacle includes a tubular member that has a retaining member adapted to engage with a post member of a deployment system such that when the post member of the deployment system is inserted into the receptacle the retaining member engages the post member so that the suture anchor is retained on the deployment system. The helical portion of the suture anchor is typically formed from a coiled wire having a sharpened tip such that when rotated the sharpened tip pierces and engages tissue. The coiled wire is preferably formed of a biocompatible, implantable material. Numerous suitable materials exist which include metals such as stainless steel, CoCr, polymers such as nylon, peek, PET, ABS, polycarbonate, biodegradable materials such as PDO, PGA, PCL, blends, bioglass and others. An elongate suture having proximal and distal ends is fixedly coupled to the suture eyelet such that rotation of the suture anchor by an attached deployment system causes the receptacle and helical portions to rotate without rotating the eyelet portion which keeps the elongate suture from winding on the deployment system and becoming entangled.

A plurality of like suture anchors may be used to perform a tissue reconfiguration procedure. While the distal end of the suture is fixedly secured to the first suture anchor, additional suture anchors are threaded onto the suture through the suture anchor eyelets. The distal end of the suture is provided with an end structure that restricts its movement against the suture retainer of a distalmost first suture anchor. Such end structure may include an enlarged knot or an attached bead that function as a stop against the suture retainer; alternatively, the end structure may be directly attached to the suture retainer via tying thereto.

There is provided a suture anchor having proximal and distal portions wherein the distal portion of the suture anchor takes the form of a coil. The distalmost portion of the coil has the sharpened tip capable of piercing tissue. The coil has a longitudinal length that is preferably chosen for the tissue in which it is to be placed. For instance, stomach tissue may have a thickness that ranges between 5 mm to 8 mm which includes a mucosal layer and a muscular layer. A corresponding suture anchor coil portion may have a longitudinal length that is approximately 8 mm, so that when the tissue is engaged by the coil portion, the coil portion can be securely anchored in the muscular layer without extending through the stomach wall and engaging tissue beyond the stomach wall. In another example, the suture anchor has a length that is suitable for use in the colon. Typically colon tissue may have a thickness that ranges between about 0.2 mm to 5 mm including the mucosa and muscular layers. A corresponding suture anchor coil suitable for colon tissue may have a longitudinal length of about 2 mm to 3 mm.

There is provided a suture anchor having proximal and distal portions where the distal portion takes the form of a coil that includes a beneficial coating. The coating may take the form of a material that is capable of swelling. For example, as a suture anchor coil (without the beneficial coating) is being anchored into tissue, the distal portion of the coil is piercing tissue with more proximal portions of the coil following. This process may enlarge the path in the tissue taken by the coil resulting in a suture anchor that is loosely secured to the tissue. Using a suture anchor coil having a swellable coating, the loosely secured suture anchor will become more firmly anchored as the coating swells and fills the enlarged path created by the coil. Additionally, should the coil portion of the anchor extend though the tissue wall, the swellable coating would reduce or eliminate the risk of fluid passing through the path created by the suture anchor. Alternatively the beneficial coating may include therapeutic compounds or agents such as antibacterials, antifungals, antivirals, and antibiotics to prevent or minimize infections. Other forms of the beneficial coating may include therapeutic compounds or materials that may accelerate the healing response of the associated tissue and or defect.

A suture anchor deployment system is provided for deploying a plurality of the suture anchors in sequence in a surgical procedure. The deployment system is preferably adapted for endoscopic or laparoscopic use, but may also be used in open surgical procedures.

The deployment system includes a proximal handle, a delivery member having proximal and distal ends, the proximal end of the delivery member rotatably coupled to the handle, and a suture anchor engaging post at the distal end of the delivery member. The delivery member preferably takes the form of an elongate torqueable shaft. The elongate shaft may be formed from a flexible cable, wire, tubular catheter, or advanced construction as described in co-owned U.S. Pat. No. 10,238,411 to Mitelberg et al. A suture anchor is removably coupled to the delivery member post for delivery to a target site. The deployment system may also include a sheath that extends over the delivery member and the attached suture anchor so that the sharp end of the suture anchor is prevented from damaging the channel of a flexible endoscope when delivering the suture anchor to a target site within the body. The sheath may be retractably coupled to the deployment system or may be a separate liner that is inserted through the instrument channel of the endoscope to act as a protective barrier between sharp aspects of the suture anchor and the wall of the instrument channel. Once the suture anchor is positioned adjacent a target tissue site, manipulation of the handle results in rotation of the elongate shaft to cause the helical portion of the suture anchor to rotate, thereby engaging the tissue at the target site. If after engaging tissue a different target site is chosen, the handle can be manipulated to rotate the shaft in the opposite direction, thereby causing the suture anchor to rotate in the opposite direction and disengage from the previously engaged tissue. At this point the suture anchor can be repositioned at the new target site and rotationally engage the tissue. Once the suture anchor has been properly positioned, the suture anchor and delivery member post may be moved relative to each other to disengage the post from the suture anchor. A second sheath that extends over the elongate shaft, but not over the suture anchor, can be advanced over the elongate shaft such that the distal end of the second sheath applies a force against the proximal end of the suture anchor to separate the suture anchor from the delivery member post. Once a first suture anchor has been deployed at a target site, the deployment system can be reloaded with a second suture anchor engaging the post member of the delivery member. As previously mentioned the second suture anchor is threaded onto the elongate suture through the suture eyelet. The second suture anchor can then be positioned at a target site and rotated to engage tissue (without the suture wrapping around the delivery member). After deployment of the second suture anchor, additional suture anchors may be loaded onto the delivery member and deployed as needed. Once the last suture anchor has been deployed, a cinch device (such as disclosed in U.S. Pat. No. 8,540,735 to Mitelberg et al., herein incorporated by reference) may be threaded over the suture and used to draw appropriate tension on the suture (drawing the suture anchors and associated tissue together) to reconfigure the tissue and then fired to maintain the tension and cut away excess suture.

The additional suture anchors may be removably mounted on a card or other member that attaches to the endoscope. The suture anchors, in the mounted configuration, are pre-threaded with the suture. The suture anchors are each provided in a removable plug that can be individually released from the card and manipulated to load the suture anchor on the delivery member post.

In an embodiment, the delivery member and attached suture anchor are sized to extend within the working channel of an endoscope. In the same embodiment, the delivery member, and any sheaths are all sufficiently flexible for use within the working channel of an endoscope that extends through a tortuous path, and particularly through the working channel of an endoscope that is retroflexed.

In use, the deployment system loaded with a first suture anchor is advanced through or pre-positioned within a working channel of an endoscope or lumen. In one method, the endoscope is positioned within a natural body orifice, such as the gastroesophageal tract, and has its distal end located within the stomach. The distal end of the deployment system is advanced out of the working channel, and the sheath protecting the distal end of the suture anchor is retracted so that the distal most end of the suture anchor is placed against a first target tissue location in which the first suture anchor is to be deployed. As the suture anchor helical portion contacts the first target tissue location, the first suture anchor is rotated to cause the helical portion of the suture anchor to pierce and engage tissue. If placement of the suture anchor is satisfactory, the suture anchor is detached from the deployment system to remain at its tissue engaged location.

The deployment system is then removed from the working channel of the endoscope and a second suture anchor is loaded onto the distal end of the deployment system. The deployment system is then re-inserted into the endoscope working channel and the distal end of the deployment system is then moved to a second target tissue location, and the process is repeated to engage tissue and deploy a subsequent suture anchor. The process is repeated as necessary to locate suture anchors at various locations suitable for a therapeutic treatment.

The suture anchors can be deployed in various patterns to effect various tissue approximations. By way of example only, the suture anchors can be positioned in a zig-zag pattern, a rectangular pattern, a circular pattern, or partially-within and partially-outside a defect and then cinched to close the defect. In addition, the anchors can be deployed to secure an implant such as a feeding tube, a stent, a gastric balloon, or can be used as markers without a suture.

Once the suture anchors have been deployed into the tissue, the deployment system can be withdrawn from the working channel and over the suture. A cinch device is then advanced over the suture, preferably through the same working channel. The suture is tensioned to drawn the suture through the suture anchors and consequently the first, second, etc. target tissue locations into apposition. Once the appropriate tension is applied to achieve tissue reconfiguration, the cinch is secured to the suture retain to the tissue reconfiguration. Alternatively, no cinch is required and the suture may be tied to retain the tension thereon.

The suture anchor deployment system provides several advantages. It can be deployed through a working channel of a conventional endoscope, and requires no modification to the endoscope. The deployment system does not increase the overall diameter of the distal end of the endoscope.

BRIEF DESCRIPTION OF THE DRAWINGS

FIG. 9A is a side elevation view of a suture anchor deployment system according to another embodiment.

FIG. 9B is a longitudinal section view of the suture anchor deployment system across line 9B-9B in FIG. 9A.

FIG. 10 is a partially transparent side elevation view of the distal end of the delivery device of suture anchor deployment system of FIG. 9A, shown without suture anchor and suture.

FIG. 11 is a partially transparent side elevation view of the distal end of the delivery device of suture anchor deployment system of FIG. 9A, shown with suture anchor and suture.

FIG. 25-27 show another method of using the suture anchor deployment system to correct a defect in the GI tract.

FIG. 28 shows another method of using the suture anchor deployment system to correct a defect in the GI tract.

FIG. 29 shows yet another method of using the suture anchor deployment system to correct a defect in the GI tract.

DETAILED DESCRIPTION OF THE PREFERRED EMBODIMENTS

With reference to the following description, the terms "proximal" and "distal" are defined in reference to the hand of a user of the device, with the term "proximal" being closer to the user's hand, and the term "distal" being further from the user's hand such as to often be located further within a body of the patient during use. Further, in accord with a general description of the system and its exemplar use, described in more detail below, the system is provided and used to target tissue, deploy a suture anchor into tissue, and reconfigure the anchored tissue. Such targeting, fastening and reconfiguring are preferably, though not necessarily, performed in conjunction with a surgical scope, such as a laparoscope or an endoscope. In embodiments described herein, the steps may be used to reconfigure tissue through or with the aid of an endoscope in which the instrument acting to reconfigure the tissue are inserted through a natural orifice, namely the gastroesophageal pathway, preferably without incision to either the dermal or internal tissues of a patient in order to effect for passage of the required instruments. Specifically, it is recognized that piercing the tissue for insertion of a fastener does not effect an incision in the tissue.

Figure 1:
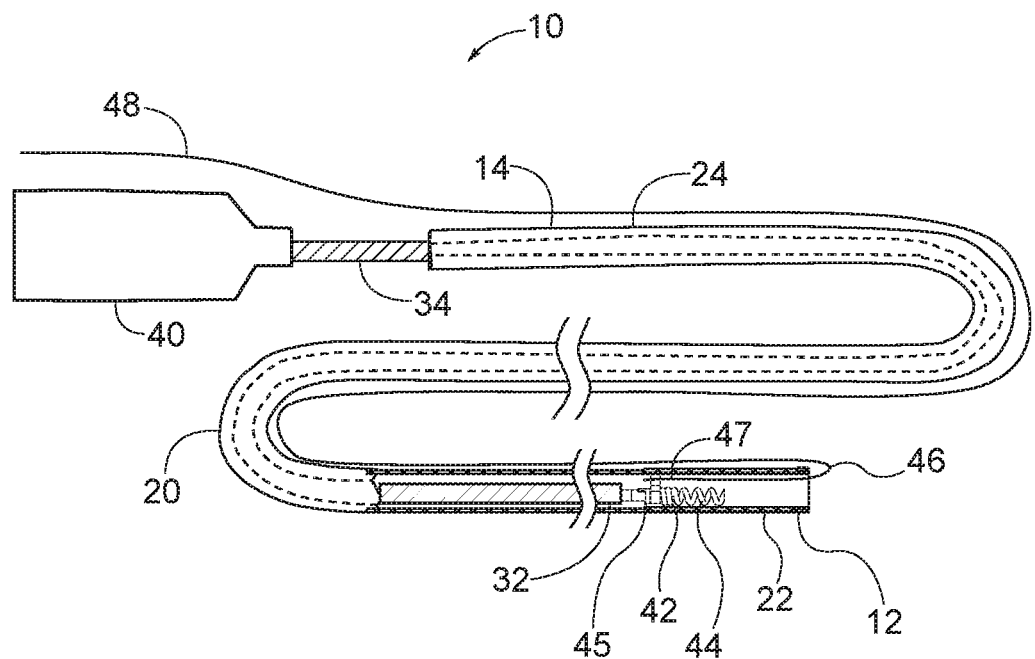
FIG. 1 is a broken side view of a suture anchor deployment system.
Figure 2:
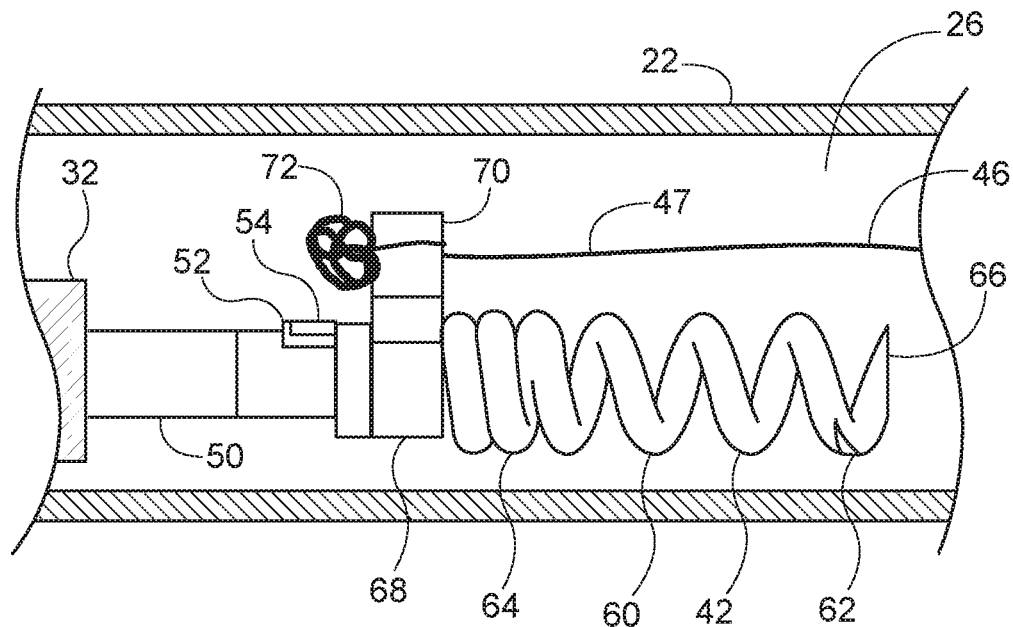
FIG. 2 is an enlarged partial sectional side view of the distal portion of the suture anchor deployment system.
Figure 3:
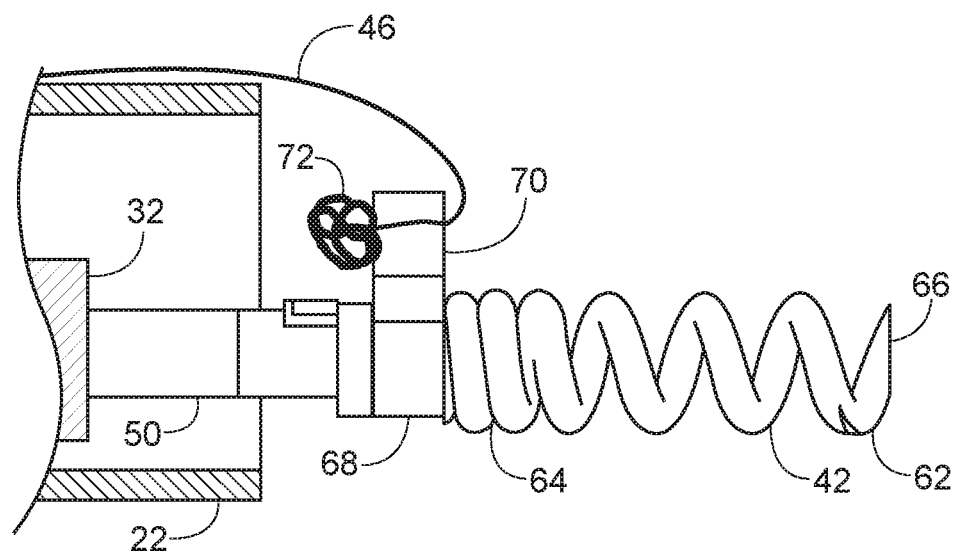
FIG. 3 is an enlarged side view of the suture anchor extending from the distal end sheath of the suture anchor deployment system.

Turning now to FIGS. 1 through 3, an embodiment of a tissue approximation system 2 is shown. The tissue approximation system 2 is intended to be delivered sterile for use during a single medical procedure and then disposed of at the end of the procedure. The tissue approximation system 2 is particularly adapted for catheter-based endoscopic approximation of soft tissue in the gastrointestinal (GI) tract. The tissue approximation system 2 includes a plurality of tissue anchors 42, an anchor delivery system 10 to implant the anchors 42 at respective tissue locations in the GI tract, and a suture element 46 that joins the plurality of tissue anchors 42. The tissue approximation system 2 preferably also includes a suture cinch system, for example, as described in U.S. Pat. Nos. 8,540,735 and 9,788,831, or US Pub. No. 2017/0086818, which are hereby incorporated herein in their entireties, to tension the suture 46 and thereby draw the plurality of implanted tissue anchors 42 toward one another and further retain the suture 46 in the cinched configuration. The elements are described in more detail below.

In an embodiment, the delivery system 10 includes a distal region 12, proximal region 14, an elongate sheath member 20 having a distal end 22, a proximal end 24 and a lumen 26 extending there through. A delivery member 30 having a distal end 32 and a proximal end 34 is slidably positioned within lumen 26 of sheath member 20. Delivery member 30 takes the form of an elongate flexible torqueable shaft having a handle member 40 coupled to proximal end 34. Delivery member 30 is preferably formed of a cable, however, other torqueable constructions, such as those found in catheters and guidewires may also be suitable. A suture anchor 42 is detachably coupled to the distal end 32 of delivery member 30. Suture anchor 42 has a distal end 44 and a proximal end 45 and is coupled to an elongate suture 46. Suture 46 has a distal end 47 which is coupled to suture anchor 42 and a proximal end 48 which adjacent the proximal region 14 of system 10.

FIGS. 2 and 3 show an enlarged view of the distal region 12 of deployment system 10. The distal end 32 of delivery member 30 includes an engagement post 50 having a rotation key 52. The rotation key 52 of the delivery member is adapted to engage the anchor rotation key 54 of suture anchor 42 when the suture anchor is attached to the delivery member.

In an embodiment of suture anchor 42, the anchor 42 includes a distally located coil 60 having a distal end 62, a proximal end 64 and a distal tip 66. Coil 60 is preferably formed from a stainless steel wire although other metals such as CoCr, nitinol, titanium, plastics such as nylon, peek, PET, ABS, polycarbonate, and biodegradable materials such as PDO, PGA, PCL, blends, bioglass may also be suitable.

The wire used to form the coil is preferably round, however, other non-circular cross-sections such as "D" shapes, ovals, rectangular, triangular and polygonal shapes may be suitable for forming the coil. The diameter of the wire may range from 0.001" to about 0.050" and is largely dependent upon the particular tissue characteristics for which the coil will engage. The diameter of the coil is generally dependent upon the wire diameter and the diameter of the mandrel used for winding. The coil diameter typically ranges from 0.030" to about 0.150" and is also dependent upon on the type of tissue and size of the endoscope channel. Positioned proximal to coil 60, suture anchor 42 also includes a collar 68 that is fixedly coupled to a suture eyelet 70. Collar 68 and suture eyelet 70 are configured to be rotatable about the longitudinal axis of the suture anchor. Suture eyelet 70 is coupled to the distal end 47 of suture 46 preferably retained through a tied knot 72 or other equivalent means such gluing or heat forming.

Figure 4A:
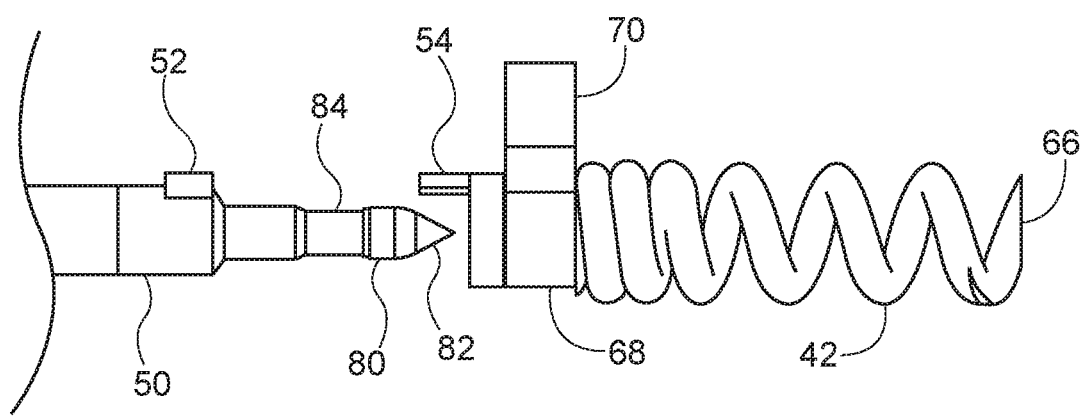
FIG. 4A is an enlarged side view of a delivery member distal end and a suture anchor.
Figure 4B:
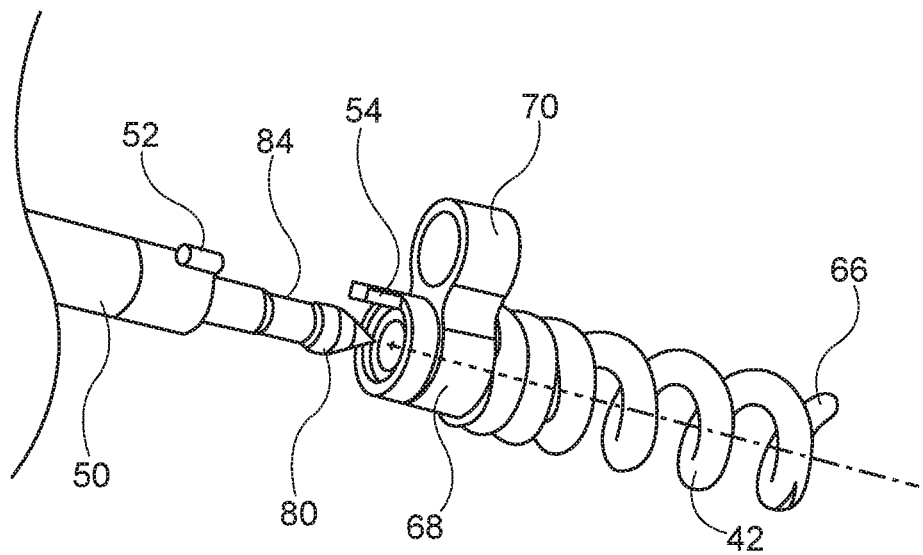
FIG. 4B is an enlarged perspective view of a delivery member distal end and a suture anchor.
Figure 4C:
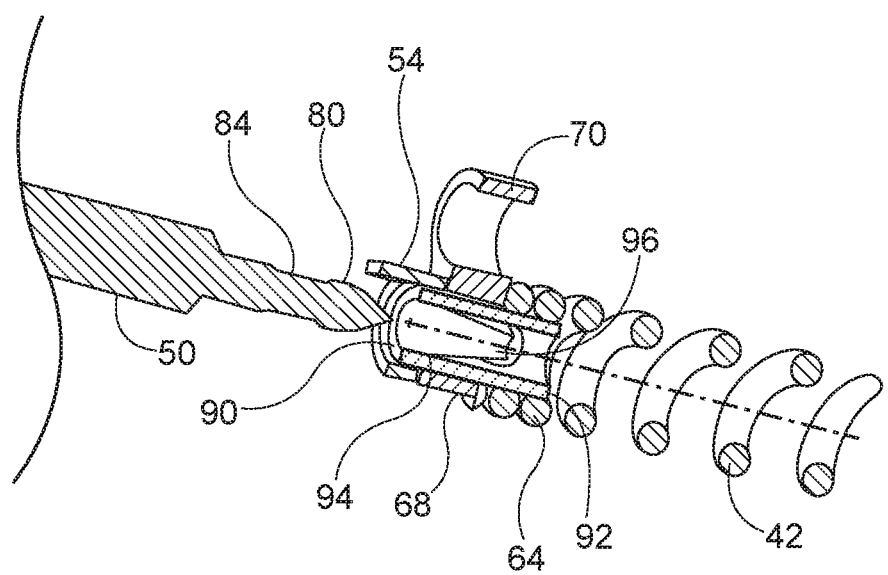
FIG. 4C is an enlarged perspective partial sectional view of a delivery member and a suture anchor.

FIG. 4A through 4C illustrate various enlarged views of the distal end of delivery member 30 and a detached suture anchor 42. As shown in FIG. 4A, engagement post 50 of delivery member 30 has an engagement post head 80 with a distal tip 82 which is tapered and an engagement post neck 84. Engagement post head 80 is bulbous and has a diameter greater than the diameter of neck 84. FIG. 4C illustrates the alignment of engagement post 50 and suture anchor 42 prior to engagement. Suture anchor 42 includes engagement receptacle 90 which extends proximally from coil 60 where distal portion 92 is fixedly secured to coil proximal end 64, preferably by laser welding or other suitable joining technique. Proximal portion 94 of engagement receptacle 90 is shown adjacent anchor rotation key 54. Engagement receptacle 90 is a tubular member and has a retaining tab 96 cut from the wall. Retaining tab 96 is normally angled towards the central axis of engagement receptacle. Retaining tab 96 acts as a live hinge so that when engagement post head 80 is inserted into receptacle 90, tab 96 is deflected upward allowing head 80 to pass tab 96. Retaining tab 96 then moves to its normally angled position where it rests on engagement post neck 84. This arrangement between the retaining tab, post head and post neck, removably couples the suture anchor and delivery member when engaged. Anchor rotation key 54 is fixedly coupled to engagement receptacle 90 preferably through welding or other suitable joining technique.

Figure 5A:
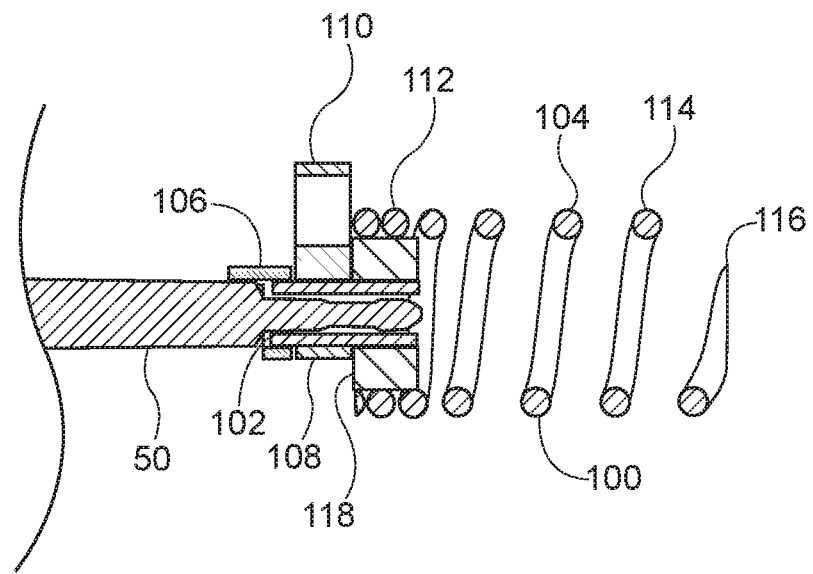
FIG. 5A is an enlarged partial sectional side view of a delivery member distal end and an alternative suture anchor embodiment.
Figure 5B:
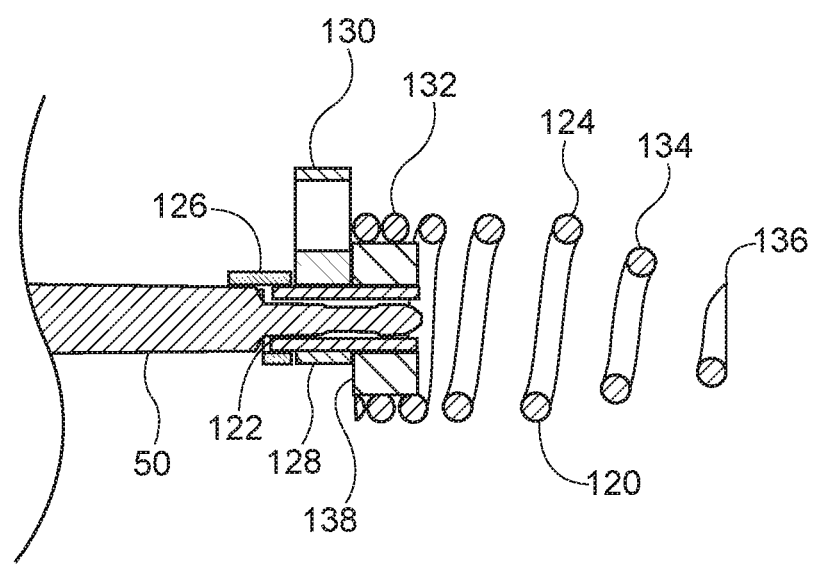
FIG. 5B is an enlarged partial sectional side view of a delivery member distal end and another alternative suture anchor embodiment.

The construction of alternative suture anchor embodiments are illustrated in FIGS. 5A and 5B. FIG. 5A shows a partially sectioned side view of suture anchor 100 that share numerous similarities to anchor 42. Anchor 100 includes a proximally positioned engagement receptacle 102 and a distally positioned coil 104. An anchor rotation key 106 is fixedly coupled to engagement receptacle 102. Collar 108 and suture eyelet 110 are positioned on and rotatable about engagement receptacle 102 distal to rotation key 106 and proximal to coil proximal end 112. Coil 104 has a distal end 114 having a sharpened distal tip 116. Coil 104 is fixedly coupled to engagement receptacle 102 through a spacer member 118. Spacer member 118 is preferably welded to receptacle 102 and coil proximal end 112. Coil proximal end 112 has a closer wound pitch than the distal end 114 to facilitate attachment to receptacle 102. Distal end 114 has a fairly open pitch to allow the coil to easily engage tissue when rotated. Spacer member 118 is formed of a biocompatible material and enables the modification of the suture anchor to use a coil that has a diameter substantially larger than the diameter of the engagement receptacle. Being able to vary the diameter of the coil and coil pitch allows for suture anchors to be created that are suited for different tissue consistencies and thicknesses.

FIG. 5B shows a suture anchor 120 similar in construction to suture anchor 100. Anchor 120 includes a proximally positioned engagement receptacle 122 and a distally positioned coil 124. An anchor rotation key 126 is fixedly coupled to engagement receptacle 122. Collar 128 and suture eyelet 130 are positioned on and rotatable about engagement receptacle 122 distal to rotation key 126 and proximal to coil proximal end 132. Coil 124 has a distal end 134 having a sharpened distal tip 136. Coil 124 is fixedly coupled to engagement receptacle 122 through a spacer member 138. Spacer member 138 is preferably welded to receptacle 122 and coil proximal end 132. As shown in FIG. 5B, coil 124 tapers towards distal tip 136. This taper may aid in deploying suture anchor 120 in tissues that have a dense or tough consistency.

Figure 6A:
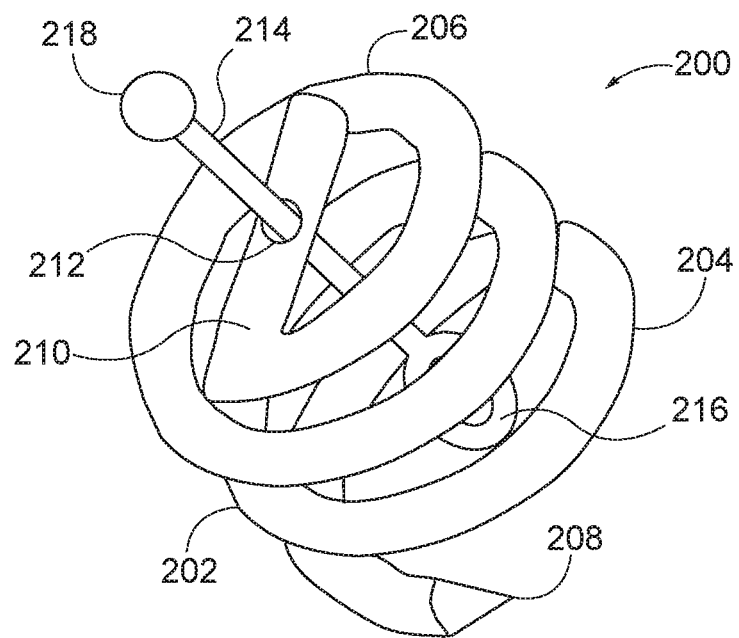
FIG. 6A is an enlarged perspective view of still another suture anchor embodiment.
Figure 6B:
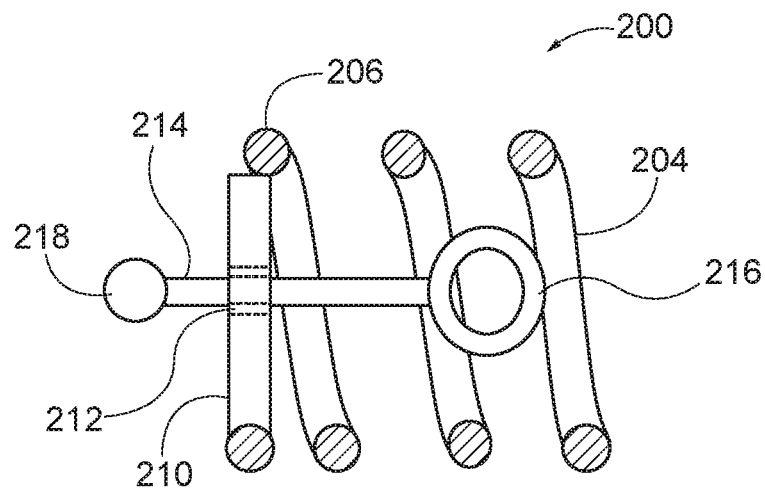
FIG. 6B is a partially sectioned side view of the suture anchor embodiment shown in FIG. 6A.

Turning now to FIGS. 6A and 6B, another suture anchor embodiment having a construction similar to previous suture anchors is shown. FIG. 6A illustrates a perspective view of suture anchor 200 that includes coil 202. Coil 202 has a distal region 204 and a proximal region 206. Distal region 204 includes a distal tip 208 adapted to pierce tissue. Proximal region 206 includes a cross member 210 that generally crosses the diameter of coil 202 creating a "D" shaped opening. Cross member 210 has an aperture 212 that is positioned at or near the center of the diameter of coil 202. Positioned through aperture 212 is an eyelet shaft 214 that has a distally positioned suture eyelet 216 and a proximally positioned retention bead 218. As shown in FIGS. 6A & 6B, suture eyelet 216 is positioned within the interior of coil 202 and is rotatable relative to coil 202. Suture eyelet 216 is also repositionable along the longitudinal length of coil 202 due to the sliding configuration of eyelet shaft 214 relative to cross ember 210. The sliding ability of the eyelet shaft and the rotating ability of the suture eyelet are important features for successful placement of suture anchor 200. The deployment of suture anchor 200 requires a deployment system similar to deployment system 10 with some modifications. The engagement post of the delivery member would be modified to have a "D" shape to engage the "D" shape formed by the cross member (not shown). While this construction allows for the suture anchor to be placed on the engagement post, additional retention features can be added to make the engagement between the delivery member and suture anchor more secure. Other embodiments of suture anchors will be described below.

When in use at a target tissue location, the suture anchor positioned on the delivery member includes an elongate suture secured to the suture eyelet. In an embodiment, the suture is 3-0 polypropylene suture, but can be any other suitable suturing material, including polymer mono filaments, polymer multi-filaments, polymer braids, metal wires, metal multistrand constructs, metal braids, polymer-metal combinations, natural biomaterials, and any other suitable suturing materials.

When the delivery member handle is rotated, the engagement post rotates causing the coil of the suture anchor to rotate. As the coil rotates, the coil distal tip engages tissue and advances deeper into the tissue. The suture secured to the suture eyelet follows the helical gap between coil winds as the coil is rotated into the tissue. When the suture eyelet contacts tissue it generally remains stationary as the rotating proximal coil end approaches the suture eyelet. The rotating ability of the suture eyelet keeps the suture adjacent the deployment system from winding onto the delivery member or otherwise becoming entangled. The sliding ability of the eyelet shaft allows the suture eyelet to move from the distal end of the coil to the proximal end of the coil signifying that the coil has been fully anchored within the tissue.

Now, in accord with one method of using the deployment system 10 (other methods are described hereinafter), an endoscope is advanced through a natural body orifice, such as the gastroesophageal tract, so that its distal end is located within a body cavity such as the stomach. The distal portion of the deployment system 10 is advanced through or pre-positioned within the working channel of the endoscope. Alternatively, the deployment system may be advanced through a peripheral lumen external of the endoscope.

Figure 7A:
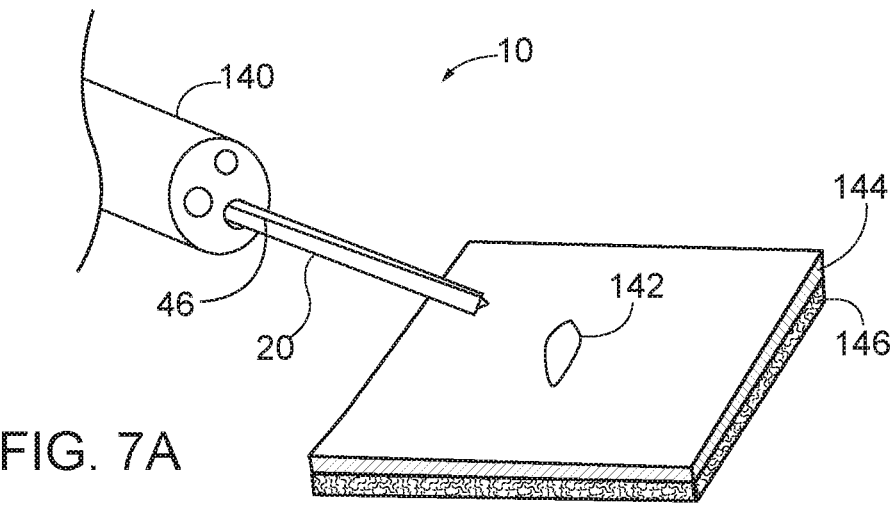
FIGS. 7A through 7H illustrate a use of the suture anchor deployment system, with FIG. 7A showing the distal end of the deployment system extending through an endoscope adjacent tissue having a tissue defect, FIG. 7B showing a retracted deployment system sheath exposing a connected suture anchor, FIG. 7C showing rotation of the deployment system such that the suture anchor engages tissue at a first location, FIG. 7D showing the release of a first suture anchor and the distal end of the deployment system with a second suture anchor extending from the endoscope, FIG. 7E showing the deployment system with a second suture anchor positioned adjacent a second tissue location, FIG. 7F showing the second suture anchor engaging tissue at a second location detached from the deployment system, FIG. 7G showing the tensioning of suture to approximate the suture anchors to close the tissue defect, FIG. 7H showing a closed tissue defect using approximated suture anchors maintained under applied tension using a cinch.
Figure 7B:
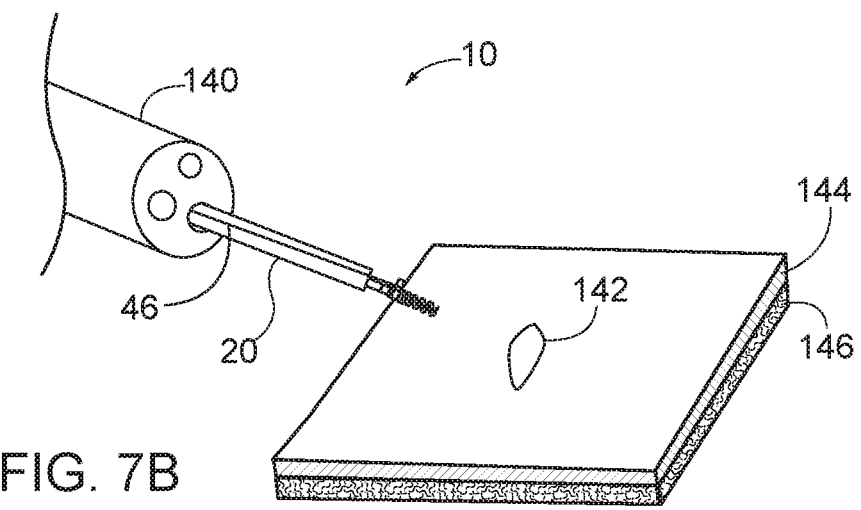
Figure 7C:
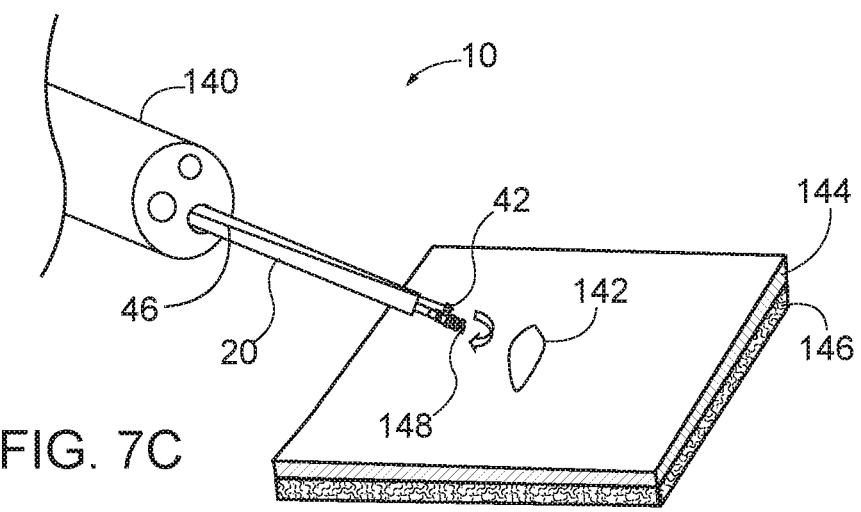

Referring to FIGS. 7A, 7B and 7C, the distal end of the deployment system, extends form the working channel of endoscope 140, the sheath is retracted revealing a first suture anchor 42 is fixedly coupled to suture 46 which is positioned near target tissue adjacent a gastrointestinal "GI" defect 142. The GI defect 142 may incorporate the mucosal layer 144 or protrude deeper and include the muscular layer 146. The distal most end of the first suture anchor 42 is placed against a first target tissue location 148 in which the first suture anchor is to be deployed. As the suture anchor coil portion contacts the first target tissue location, the first suture anchor is rotated by rotating the proximal handle of the delivery member to cause the coil portion of the suture anchor to pierce and engage tissue. Once properly placed, first suture anchor 42 is then detached from delivery member 30 and left anchored in the tissue. If placement of the first suture anchor is not satisfactory, the delivery member can be rotated in the opposite direction which will cause the coil of the suture anchor to rotate in the opposite direction and dis-engage from the tissue so that the suture anchor can be repositioned and deployed again at another location.

Figure 7D:
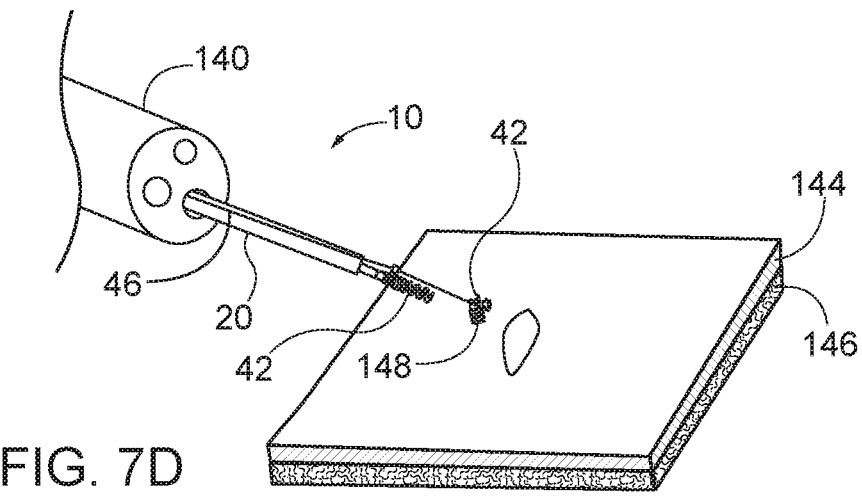
Figure 7E:
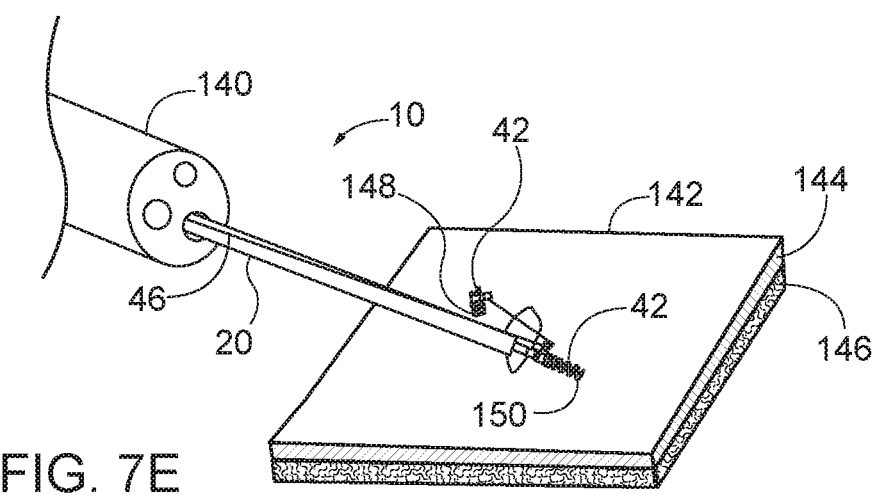
Figure 7F:
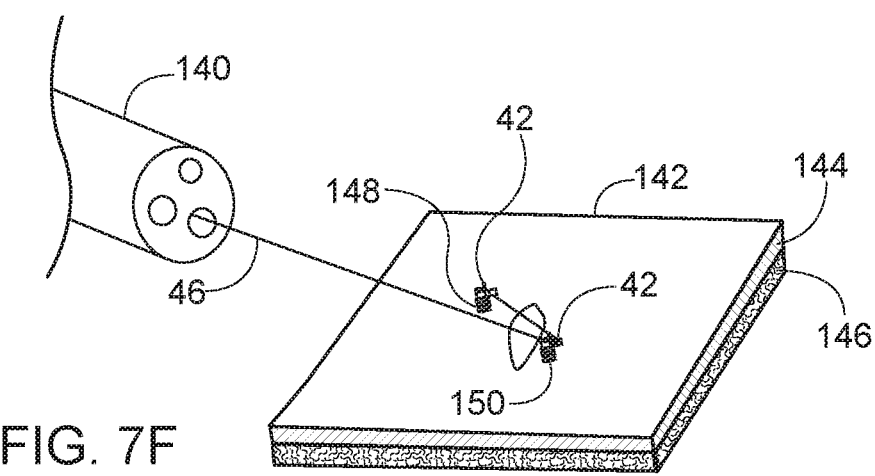

After deploying the first suture anchor, deployment system 10 is then removed from the working channel of endoscope 140 and a second suture anchor 42 (slidably coupled to suture 46) is coupled to the distal end of the deployment system. The deployment system is then re-inserted into the endoscope working channel and the distal end of the deployment system is then moved to a second target tissue location 150, and the process is repeated to engage tissue and deploy the second suture anchor 42 as shown in FIGS. 7D, 7E and 7F. The process can be repeated as necessary to deploy additional suture anchors (slidably coupled to suture 46) at various locations suitable for a therapeutic treatment.

Figure 7G:
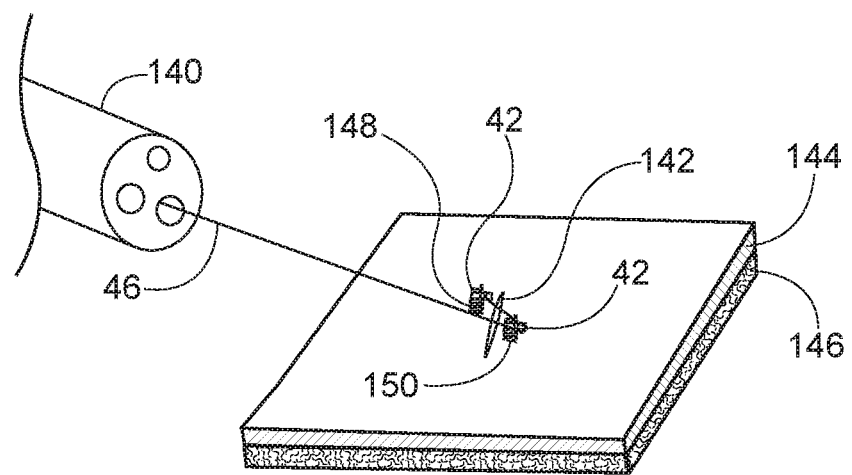
Figure 7H:
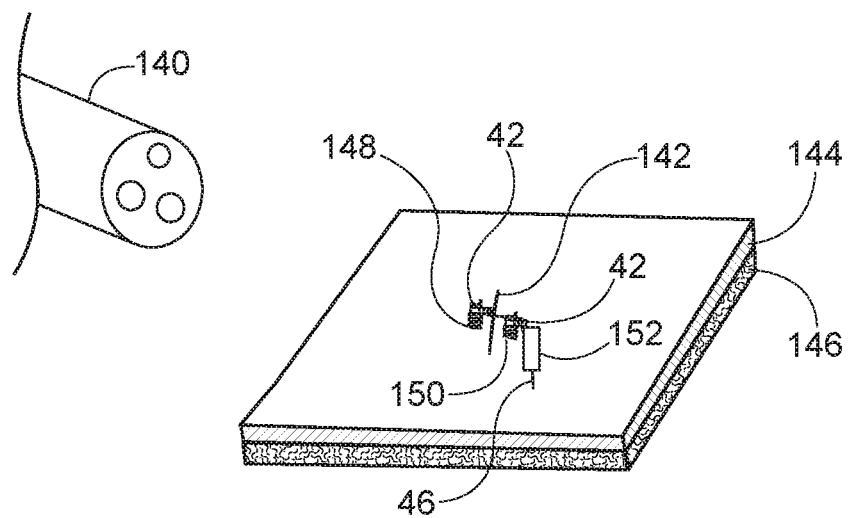

As shown in FIGS. 7G and 7H, once the suture anchors have been deployed into the tissue, the deployment system can be withdrawn from the working channel. A cinch device (not shown) is then advanced over the suture to the last deployed suture anchor location. The suture 46 is then tensioned to draw the suture through the suture anchors and consequently the first, second, etc. target tissue locations into apposition. Once the appropriate tension is applied to achieve the desired tissue reconfiguration (closure of defect 142), the cinch 152 is secured to the suture retain the tissue reconfiguration.

Figure 8:
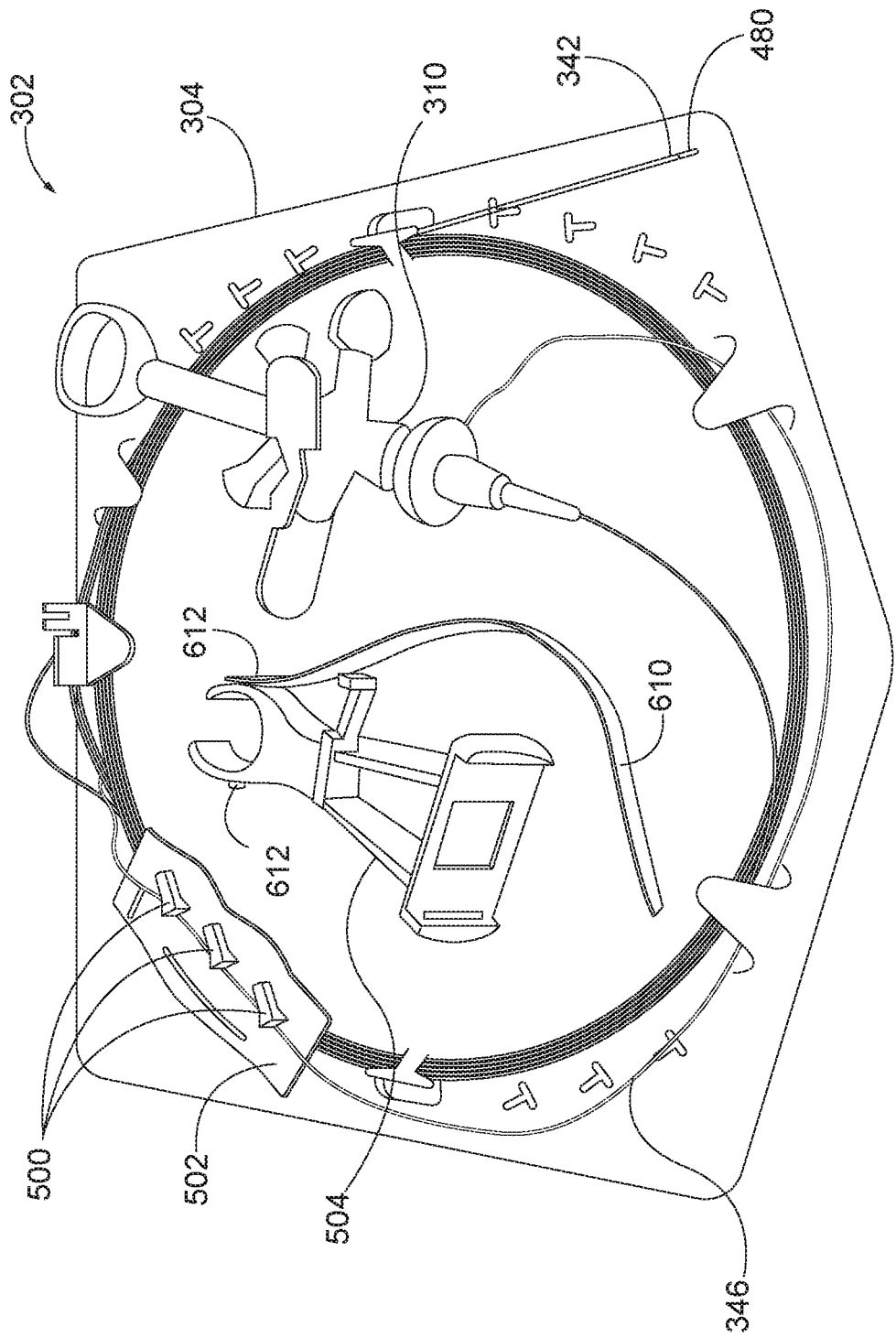
FIG. 8 is a top perspective view of a suture anchor deployment kit.

Turning now to FIG. 8, another embodiment of a tissue approximation system 302 is shown. The tissue approximation system 302 includes an anchor delivery device 310 to deliver a plurality of anchors 342 (one pre-mounted at the distal end of the delivery device and others loaded in holders 500 on a card 502), and a suture element 346 that joins the plurality of tissue anchors. The system may also include an endoscope mount 504 to mount the delivery device relative to an endoscope (not shown) during a medical procedure. The tissue approximation system preferably also includes an endoscopic channel liner 480 to function as a flexible tubular protective barrier between a working channel of an endoscope and the anchor delivery system, and particularly the sharpened anchor at the distal end of the delivery system. The delivery device, suture, suture anchors, mount and channel liner are preferably provided in a kit form 304, retained in a singular package suitable for single use. The packaged kit is preferably provided pre-sterilized in preparation for use.

Turning now to FIGS. 9A and 9B, the delivery system 310 includes a proximal actuation handle 510 including a stationary shaft portion 512 and a longitudinally displaceable spool portion 514. The shaft portion 512 includes a thumb ring 516 and an axial slot 518. A worm gear 520 is rotatably mounted within the axial slot 518. The spool portion 514 defines finger grips 515 and a drive bar 521 that extends into the slot 518. The drive bar 521 defines an inner bore 522 with a helical form. The spool portion 514 is coupled over the worm gear 520 in a closely fitting arrangement. Displacement of the spool portion 514 over the worm gear 520 causes the worm gear 520 to rotate about its longitudinal axis A. A torqueable shaft 522 is fixed at the distal end of the worm gear 520. When the worm gear rotates, the torqueable shaft 522 rotates an equal degree of rotation.

Referring now to FIGS. 9A-10, a longitudinally stiff sheath 524, such as a flat wound coil, is provided over the torqueable shaft 522. The proximal 525 end of the sheath 524 is coupled to a ferrule 526 and the distal end 528 of the sheath has a substantially flat end 530. The ferrule 526 is threadedly mounted on the distal end of the shaft portion 512 of the actuation handle 510 at threads 529. When the ferrule 526 is rotated, the ferrule 526 longitudinally displaces as it is advanced or retracted through the threads and consequently, the flat end 530 of the sheath 524 longitudinally displaces relative to a suture anchor engagement post 350 fixed to the distal end of the torqueable shaft 522. As described below, this permits controlled disengagement of the suture anchor 542 from the engagement post 350.

As an alternative to deployment via threaded displacement of the ferrule and thus the sheath, a spring-release can be provided that, upon operation, results in an automatic longitudinal displacement of the sheath by a predetermined distance sufficient to deploy the suture anchor from the engagement post 350. The spring-release is preferably operated by a push-button located on the proximal handle.

Referring to FIG. 10, the engagement post 350 has a generally cylindrical proximal first portion 534, a reduced diameter second portion 536 that receives a proximal portion of the suture anchor, a shoulder 538 between the first and second portions that functions as a stop for the suture anchor, a third portion 540 defining opposing recesses 542 that function as keyways for receiving rotational keys in the suture anchor for rotational force application, and a bulbous distal fourth portion 544 that prevents unwanted deployment until actuated disengagement of a suture anchor.

Figure 12:
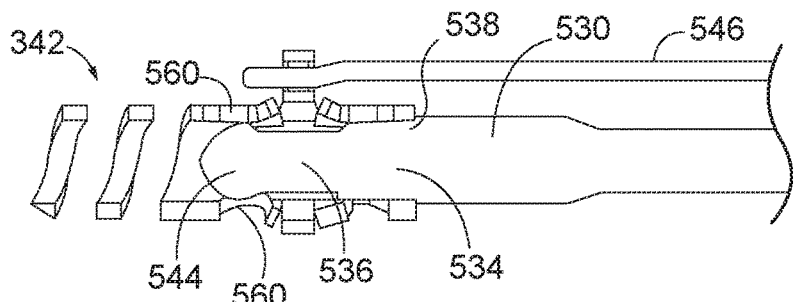
FIG. 12 is a longitudinal section view across line 12-12 in FIG. 11.
Figure 13:
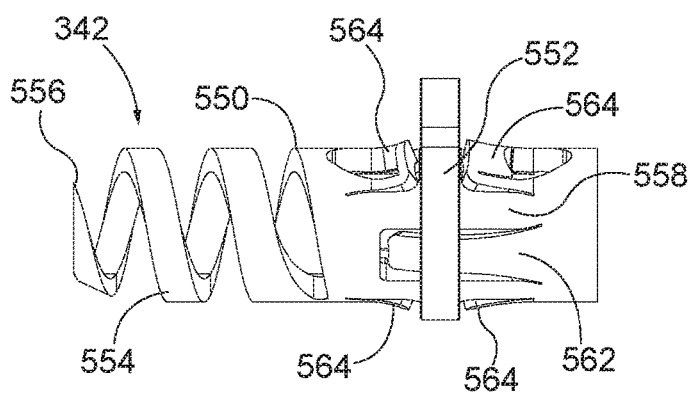
FIG. 13 is a side elevation of an embodiment of a suture anchor.
Figure 14:
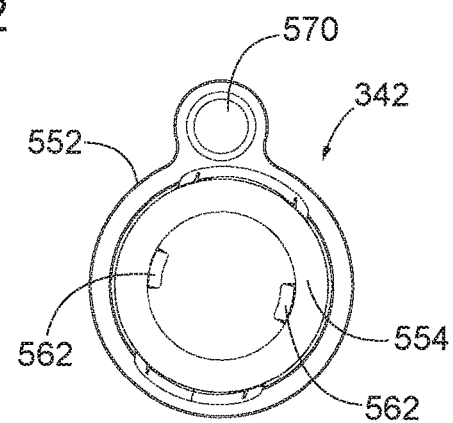
FIG. 14 is an end view of the embodiment of the suture anchor of FIG. 13.

Turning now to FIGS. 11 through 17, in an embodiment, the suture anchor 342 includes a laser cut tube 550 and an eyelet ring 552. The laser cut tube 550 defines a distal open helical coil 554 with a sharp distal end 556, and a proximal post receiver 558. In an embodiment, the open coil 554 has a length of approximately 2.5 mm. As shown in FIGS. 11 and 12, the receiver 558 is sized to be received over the second, third and fourth portions 534, 536, 538 of the post 350, but stop against the shoulder 538 defined between the first and second portions. The receiver 558 includes a pair of recesses 560 such that the receiver is adapted to receive the bulbous distal fourth portion 544 of the post, and a pair of radially-inward extending first tabs 562 forming anti-rotational keys that extend into the opposing recesses 542 on the post. The receiver also includes two pairs of radially outwardly biased second tabs 564, each pair diametrically opposed from the other, that define a circumferential channel 566. The eyelet ring 552 includes a circular first opening 568 and a second opening 570 outside the perimeter of the first opening. The circular first opening 568 is substantially the same diameter as the outer diameter of the tube 550. In assembly of the suture anchor 542, the proximal end 572 of the tube is pushed through the first opening 568 until the proximal ones of outwardly biased second tabs 564 are displaced inwards to permit the ring 552 to seat in the channel 566, and then the proximal tabs release back outwards to lock the ring 552 in its longitudinal position on the tube (i.e., between the two pairs of tabs 564). While locked on the tube 550, the ring 552 is permitted to rotate about the circumference of the tube 550. The second opening 570 receives the suture 546 therethrough. Thus, while the tube 550 can be rotated by rotation of the deployment post 350, the eyelet ring 552 and the suture 346 are independent and do not follow such rotation.

Figure 15:
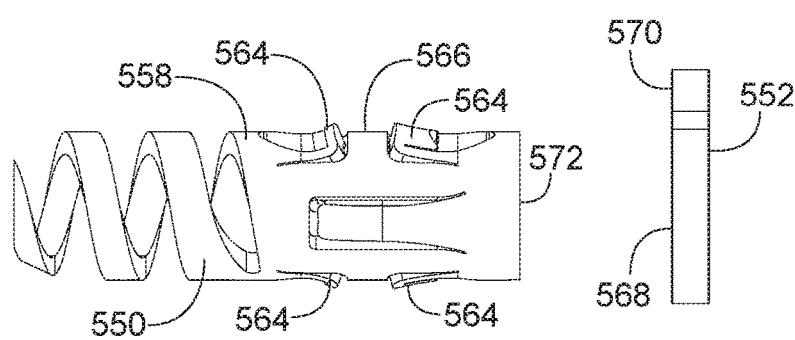
FIG. 15 is a side elevation of an embodiment of a laser cut tubular element of a suture anchor.
Figure 16:
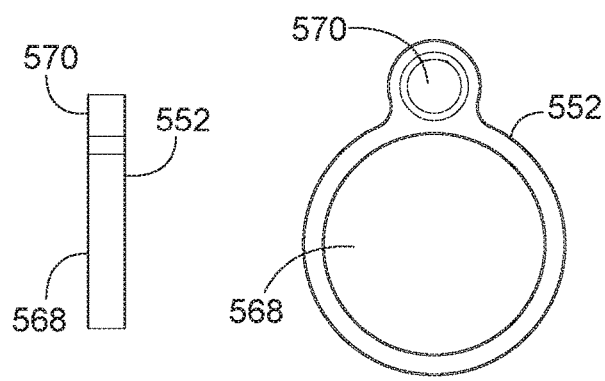
FIG. 16 is a side elevation of an embodiment of an eyelet ring for a suture anchor.
Figure 17:
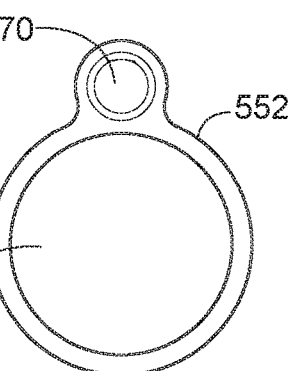
FIG. 17 is an end view of the eyelet ring of the FIG. 16.
Figure 18:
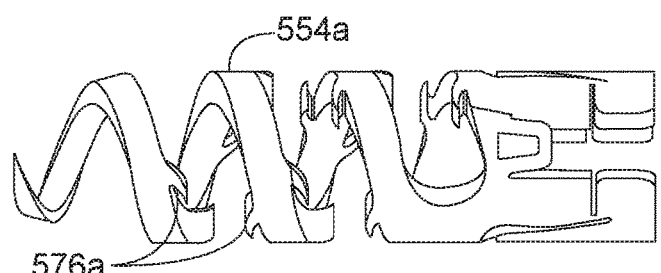
FIG. 18 is a side elevation view of another embodiment of a laser cut tubular element for a suture anchor.

As shown in FIG. 15, the laser cut tube 550 can be formed with various features. In an embodiment, the winding of the coil 554 has a flat cross-section corresponding to the wall of the tube 550; however, other cross-sectional shapes can be defined during the manufacturing process, including round and D-shaped. In addition, the coil can be formed with a constant or variable pitch. Moreover, one or both surfaces of the coil can be laser textured or textured by other means to facilitate insertion and/or tissue retention. By way of example, a laser-cut coil 554a can be formed with integrated barbs 576, as shown in FIG. 18.

An aspect of the suture anchor is that it consists of only two elements, the tube and the eyelet ring. A further aspect is that the assembly only requires that the eyelet ring be pushed onto the tube. That is, no welding, brazing, gluing, adhesive, or other bonding is required between the two components to retain them together. Another aspect is that the eyelet ring is rotatable on the tube, but longitudinally retained on the tube. Yet another aspect is that all features retaining the eyelet ring to the tube, as well as the assembled suture anchor to the deployment post are formed by laser cutting the appropriate structure into the tube.

It is recognized that various structure of the engagement post and the laser cut tube could be reversed; i.e., the engagement post could be formed of a tube and cut with various tabs, and the suture anchor could be solid and define recesses that could be engaged by the post.

Referring to FIGS. 9A, 9B and 11, the travel of the spool portion 514 along the worm gear 520, from one end to the other is adapted to cause sufficient rotation of the helical coil 554 to fully implant the coil into tissue. That is, if the coil 554 extends through 1140° of rotation, then movement of the spool portion 514 along the worm gear through the length of the slot 518 causes the flexible shaft 522 to rotate 1140°. If a procedure requires an anchor 542 with a coil 554 having a smaller angular rotation for complete implantation, then a spacer 580 (FIG. 9A) can be inserted at one end of the slot, or over one end of the spool portion to function as a stop and limit displacement of the spool portion relative to the worm gear to thereby limit the effective rotation cause by movement of the spool portion through its travel.

As indicated above, the tissue approximation system 302 includes endoscope channel liner 480. The channel liner 480 is a flexible tube adapted to be inserted into a 2.8 mm or larger working channel of an endoscope, such as a gastroscope or colonoscope, to protect the inner surface of the working channel from damage by the sharp distal ends of the suture anchors. A proximal end of the channel liner can include an enlarged opening 482, to assist in guiding the distal end of the delivery device therein. The channel liner 480 is preferably made from a combination of high density polyethylene (HDPE) and low density polyethylene (LDPE), and more preferably 80% HDPE and 20% LDPE. As an alternative, the deployment system can incorporate a retractable sheath that covers the sharpened end of the helical coil until deployment of the anchor, as described above.

Figure 21:
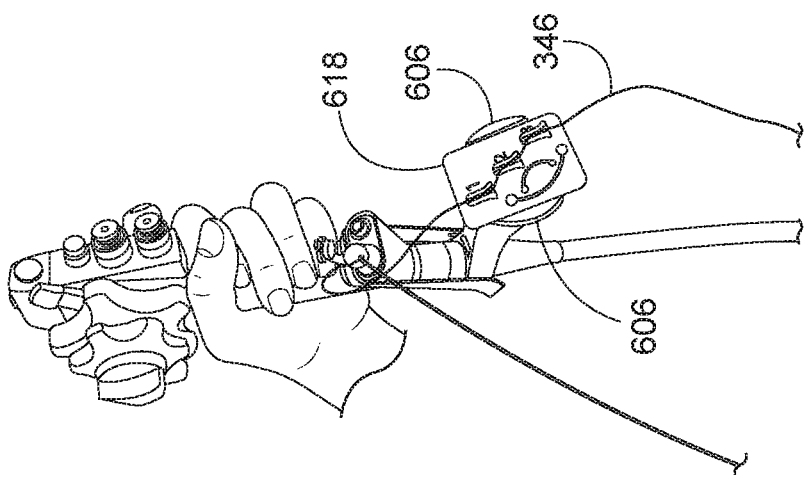
FIG. 21 is a photograph of the card in FIG. 20 shown mounted to the mount in FIG. 19.
Figure 20:
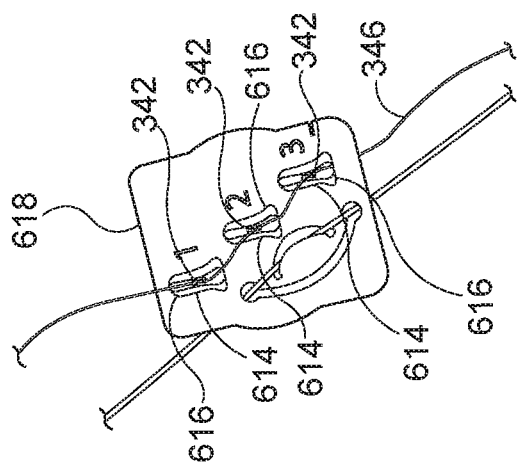
FIG. 20 is a photograph of a card storing plugs holding additional suture anchors.
Figure 19:
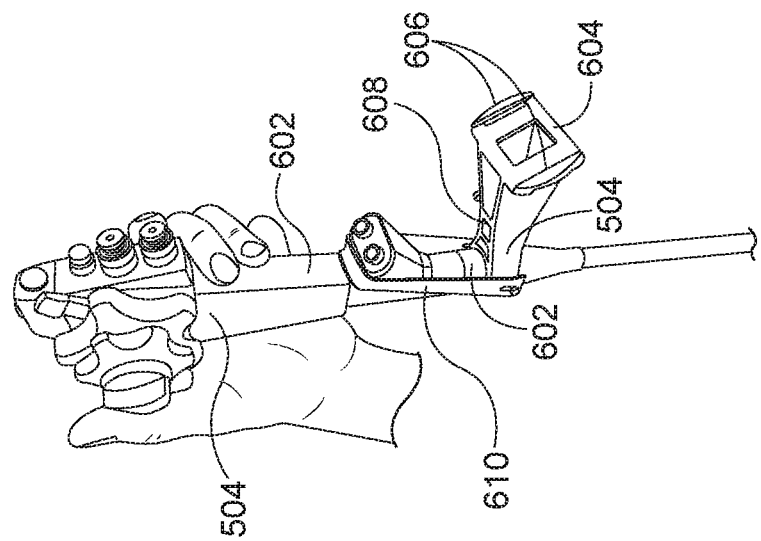
FIG. 19 is a photograph of an endoscope having a mount provided thereon for the suture anchor deployment system.

Turning now to FIGS. 8 and 19 through 21, in all embodiments, removable mount 504 may be provided to temporarily secure the delivery device 310 to an endoscope 140, and place the additional suture anchors 342 (those suture anchors that are not mounted on the deployment post 350 in the delivered configuration of the approximation system) at a convenient location for the surgeon. The mount 504 includes a support 600 adapted to be received over the endoscope adjacent the endoscope handle 602, a bracket 604 having opposing retainers 606, and an arm 608 to displace the bracket from the support. An elastic band 610 is also provided and attaches to side buttons 612 on the mount 504 (FIG. 8). The suture anchors 342 are retained in disposable plugs 614 and mounted into spaces 616 on a card 618. The card 618 is mounted into the bracket 604, held by the retainers 606 (FIG. 21). In the card-mounted configuration, the anchors 342 are pre-threaded with the suture 346. The plugs 614 can be individually released from the spaces 616 in the card 618 and manipulated by hand to load the respective suture anchor on the delivery member post 350 after delivery of a prior anchor.

Turning now, in a method of use, the components of the approximation system, generally as shown in FIG. 8, are provided as a kit, together in a sterile package. The kit is opened, and the channel liner 480 is removed and advanced into a working channel of an endoscope. (It is appreciated that deployment of the one or more suture anchors via the delivery device be performed under visualization of the scope.) The delivery device 310 is provided pre-loaded with a suture anchor 342 at its distal end, and with suture 346 securely attached at the eyelet 552. As discussed above, the suture 346 extends back along the delivery system 310 and is preferably provided pre-threaded through the eyelets of the other suture anchors.

The distal end of the delivery device 310 is advanced through the channel liner 480 in the working channel, out the end of the endoscope and toward a target tissue location. Once the tissue anchor is at the target location, the spool portion 514 is displaced toward the thumb ring 516 to result in the worm gear 520, and thus the flexible shaft 522, rotating in a direction that causes the helical coil 554 of the anchor 342 to engage into the target tissue. The speed of the rotation and engagement is controlled by the speed of translation of the spool portion 514 along the shaft portion 512 of the handle 510. If the engaged location is not ideal, the direction of the spool portion 514 can be reversed, causing counter-rotation of the suture anchor 342 and consequent disengagement of the anchor from tissue. The suture anchor 342 then can be relocated as appropriate. After successful tissue engagement by the first suture anchor 342, the ferrule 526 is advanced relative to the handle 510. As discussed above, in one embodiment, such advancement is effected by threadedly rotating the ferrule 526 relative to the shaft portion 512. As the ferrule 526 is advanced, the distal end 530 of the flat wound coil 524 advances over the flexible shaft 522 and contacts the proximal end of the suture anchor 342. Further advancement of the ferrule 526 applies sufficient force to the suture anchor 342 to deploy the suture anchor 342 from the deployment post 350, thereby separating the suture anchor 342 from the delivery system 310.

The delivery system 310 is then retracted through the channel liner 480. A plug 614 with second suture anchor 342 is removed from the card 618, advanced along the suture 346 as necessary, and pushed into engagement with the deployment post 350. The plug 614 is then removed from over the suture anchor 342 and discarded. The delivery system 310 is then delivered back down through the channel liner 480 to deploy the second suture anchor 342. The process is repeated as necessary for subsequent suture anchors until all target tissue locations have received suture anchor. The delivery system is then finally removed from the channel liner 480, and the channel liner 480 may also be removed from the working channel of the endoscope.

The tissue approximation system 302 is then preferably used with a cinching system adapted to tension the suture and thereby draw implanted suture anchors toward one another into a cinched configuration, and then retain the suture in the cinched configuration. The cinching system may be packaged together with the approximation system kit or packaged separately, as the cinching system has numerous uses beyond this application. Exemplar suture cinching systems include those described in the previously incorporated co-owned U.S. Pat. Nos. 8,540,735 and 9,788,831, and in co-owned US Pub. No. 2017/0086818.

As such, in accord with a following step method, the cinching system is threaded over the suture and delivered through the working channel, adjacent the last delivered suture anchor. Under endoscopic visualization, tension is applied to the suture to pull the tissue anchors relative to each other and achieve the intended tissue manipulation. In most instances the intended tissue manipulation includes approximating the tissue anchors such that the portions of tissue associated with the anchors are each brought into direct contact with each other to aid in the healing process. The cinching device is then actuated to secure the tissue manipulation by crimping a cinch onto the suture and cutting the suture.

Figure 24:
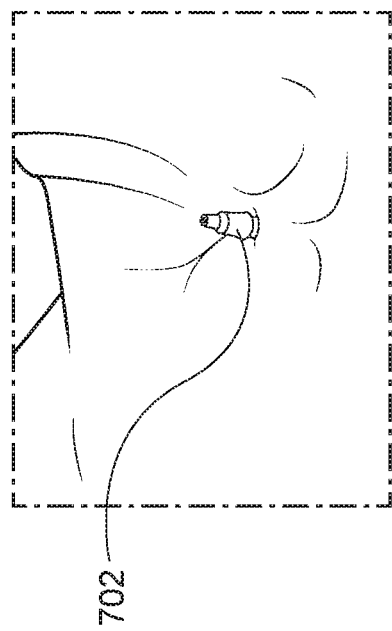
FIG. 22-24 show a method of using the suture anchor deployment system to correct a defect in the GI tract.
Figure 23:
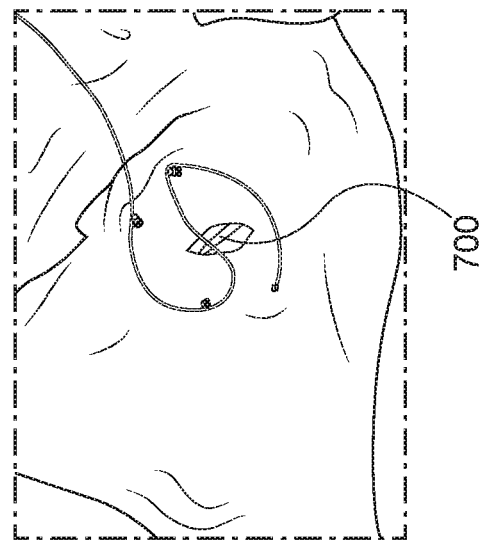
Figure 22:
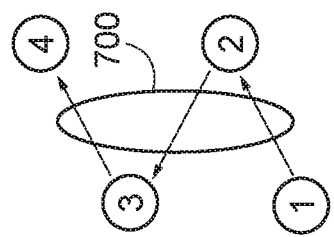

In accord with all of the above, various tissue manipulations can be performed. In one example, anchors can be positioned around a gastric defect 700 as shown in FIGS. 22 and 23. For example, the defect 700 can be a submucosal resection site or a tissue perforation. The defect 700 is closed by positioning four suture anchors such that the suture extends in a zig-zag configuration about the defect. Then, the suture is cinched and secured with cinch 702 to approximate the surrounding tissue, as shown in FIG. 24. In another example, shown in FIGS. 25 through 27, the defect 710 can be closed by placing anchors about a periphery of the defect and cinching the suture like a 'purse string'. In further examples shown in FIGS. 28 and 29, suture anchors can be positioned partially within (FIG. 28) or completely within (FIG. 29) the defect, preferably along with one or more suture anchors located outside the defect. In addition, as shown in FIG. 29, the suture path 720 can extend crosswise in two directions through and/or across the defect.

Figure 30:
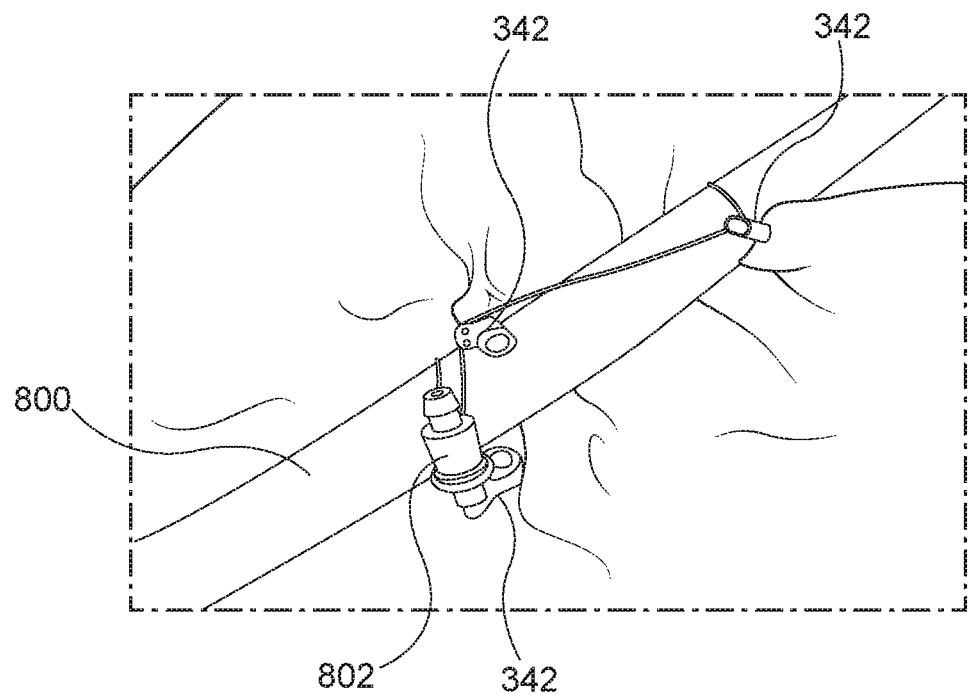
FIG. 30 shows a method of using the suture anchor deployment system to implant a feeding tube in the GI tract.
Figure 31:
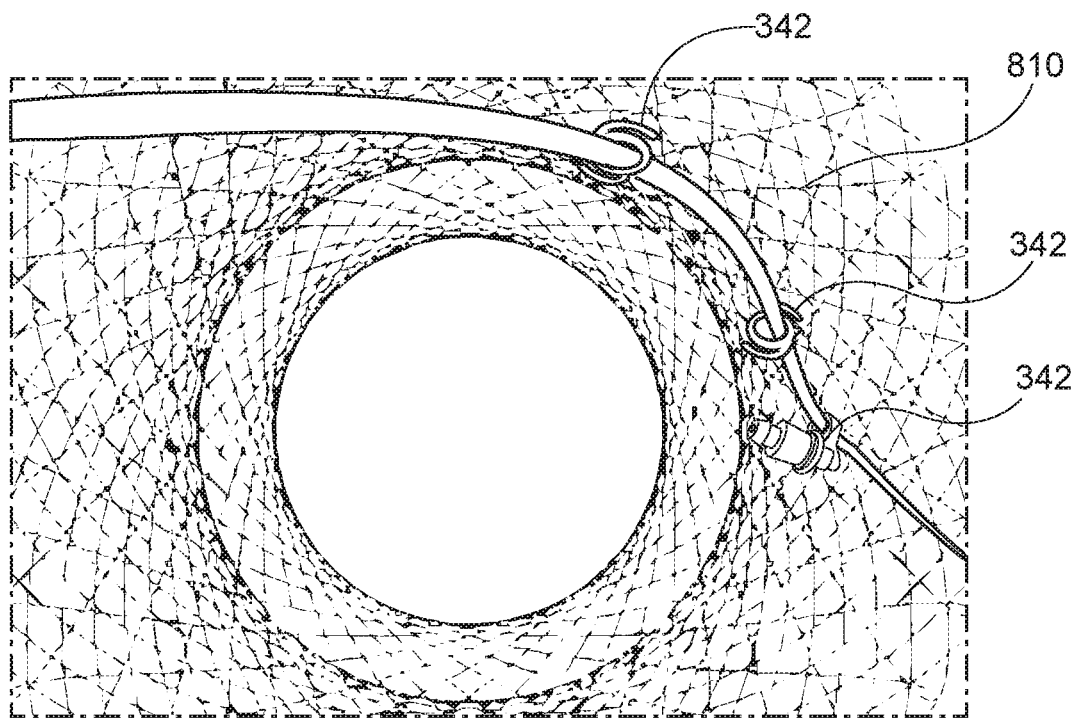
FIG. 31 shows a method of using the suture anchor deployment system to implant a stent in the GI tract.
Figure 32:
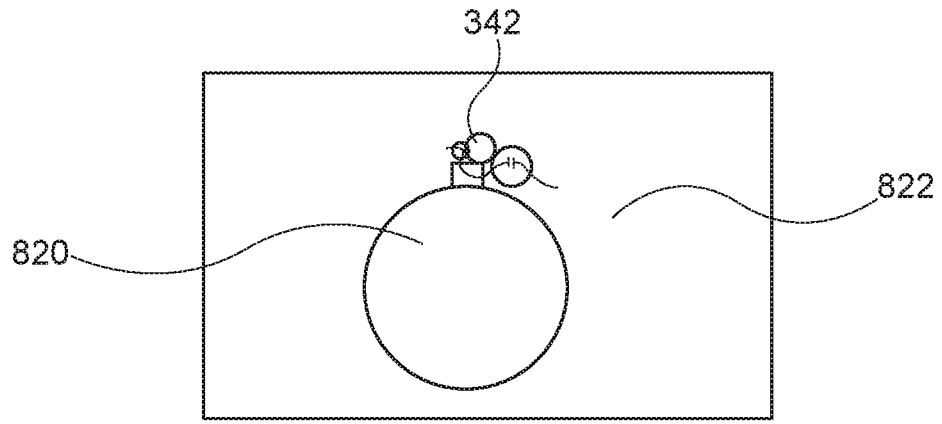
FIG. 32 shows a method of using the suture anchor deployment system to implant a gastric balloon in the GI tract.
Figure 33:
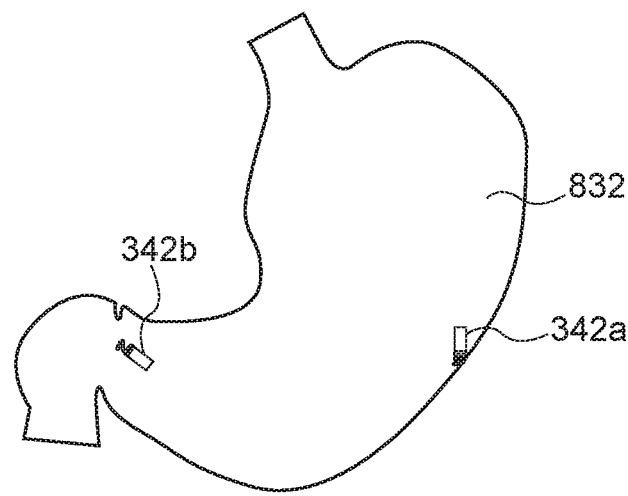
FIGS. 33 and 34 shows a method of using suture anchors to mark areas of tissue in the GI tract.
Figure 34:
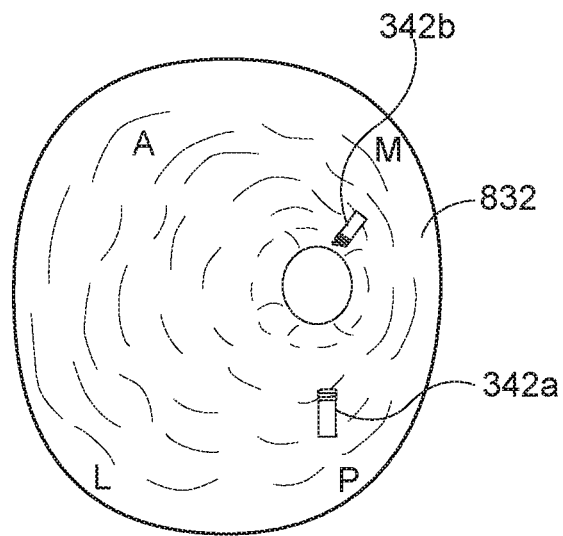

In yet other uses, the suture anchors can be used to secure an implant in the GI tract. In one such method, shown in FIG. 30, suture anchors 342 are implanted in soft tissue on either side of a gastric feeding tube 800, and then the tube is secured by tensioning and securing the suture 346 with a cinch 802. In another method, shown in FIG. 31, suture anchors 342 are positioned through the open mesh of the struts in a stent 810; tensioning the suture through the anchors and securing the tensioned suture with a cinch secures the stent to the tissue. In yet another method, as shown in FIG. 32, a single or multiple suture anchors 342 may be used to secure a gastric balloon 820 to soft tissue in the stomach 822. Turning now to FIGS. 33 and 34, the suture anchors 342 also can be used individually or in an array, but without suture, to endoscopically mark tissue in the GI tract. For example, locations for further or later investigation in the stomach 832 can be marked with suture anchors 342a, 342b. The location of the anchors can then later be identified through fluoroscopic imaging, palpation, or subsequent endoscopy.

There have been described and illustrated herein embodiments of an endoscopic tissue approximation system for deploying one or more suture anchors, embodiments of suture anchors, and methods of deploying one or more anchors, fastening tissue, and reconfiguring tissue. While particular embodiments of the invention have been described, it is not intended that the invention be limited thereto, as it is intended that the invention be as broad in scope as the art will allow and that the specification be read likewise. It is specifically intended that aspects of the various embodiments can be combined with each other. By way of example only, the barbs on the coil of one of the anchors can be provided to any of the anchors. In addition, the term 'suture' is not intended to be limiting, as it is intended to encompass any suitable tether that can join a plurality of anchors and permit the anchors to be cinched together, and can include materials not typically considered 'suture' materials. It will therefore be appreciated by those skilled in the art that yet other modifications could be made to the provided invention without deviating from its scope as claimed.

What is claimed is:

1. An endoscopic deployment system for placing a suture anchor at a site within a mammal comprising:
   an elongated flexible delivery member having proximal, intermediate, and distal regions, proximal and distal ends, an elongate shaft member having proximal and distal ends, a handle coupled to said proximal end of the shaft member, said handle including,
   i) a stationary member defining a longitudinal slot;
   ii) a movable member longitudinally displaceable over said stationary member, the movable member having a drive portion that rides in the slot; and
   iii) a worm gear rotatably mounted in the slot, said worm gear having proximal and distal ends, said drive portion of said movable member having a bore with an opening that closely accommodates said worm gear such that when said movable member is displaced over said stationary member, said worm gear is rotated and results in rotation of the proximal end of said shaft member, and rotation of said proximal end of said shaft member causes the distal end of said shaft member to rotate;
   a coupling assembly fixedly coupled to the distal region of said delivery member including an engagement post; and
   a suture anchor having proximal and distal ends, a tubular receiver having a central longitudinal axis, a coil member positioned at said distal end of said suture anchor, and a suture eyelet rotatable relative to said receiver;
   wherein:
   said delivery member is operable between a first operable configuration and a second operable configurations;
   when said delivery member is in said first operable configuration, said suture anchor is releasably coupled to said coupling assembly whereby said engagement post couples with said receiver and rotation of the distal end of the shaft member results in rotation of said suture anchor such that when said suture anchor is in contact with tissue, rotation of said distal end of said shaft member causes the coil member of said suture anchor to engage the tissue; and
   when said delivery member is in said second operable configuration, said suture anchor is detached from said coupling assembly, said delivery member being operable between said first and second operable configurations.

2. An endoscopic deployment system according to claim 1, wherein said handle is operable to rotate the proximal end of said shaft member, which results in rotation of the distal end of the shaft member.

3. An endoscopic deployment system according to claim 1, further comprising a sheath having proximal and distal ends, the sheath extending over the shaft member such that the distal end of the sheath is located proximal to the suture anchor, the handle actuatable to move the sheath distally over the shaft member so as to dislodge the suture anchor from the engagement post.

4. An endoscopic deployment system according to claim 1, further comprising a suture anchor release surface located proximal to the suture anchor, the handle actuatable to move the suture anchor release surface distal into contact against the proximal surface of the suture anchor to disengage the suture anchor from the engagement post.

5. An endoscopic deployment system according to claim 4, wherein the handle is actuated to move the suture anchor release surface by operating a spring-release or helically advancing a coupler to which the suture anchor release surface is coupled.

6. An endoscopic deployment system according to claim 1, wherein said flexible delivery member is sufficiently flexible to be positioned through a tortuous path.

7. An endoscopic deployment system according to claim 1, wherein said flexible delivery member and said suture anchor in said first operable configuration is disposed within the lumen of an elongate sheath having proximal and distal ends.

8. An endoscopic deployment system according to claim 7, wherein said elongate sheath is decoupled from said handle.

9. An endoscopic deployment system according to claim 1, wherein the distal region of said delivery member includes a first rotation key, and said suture anchor includes a second rotation key, wherein said first and second rotation keys rotationally interfere with each other.

10. An endoscopic deployment system according to claim 1, wherein said engagement post includes at least one recess, and said suture anchor includes at least one tab, and when said engagement post is coupled with said receiver, said at least one tab and at least one recess rotationally interfere such that axial rotation of said engagement post results in rotation of said suture anchor.

11. An endoscopic deployment system according to claim 1, wherein said engagement post includes one of a recess and tab, and said suture anchor includes the other of a recess and a tab, and when said engagement post is coupled with said receiver, said tab and recess rotationally interfere such that axial rotation of said engagement post results in rotation of said suture anchor.

12. An endoscopic deployment system according to claim 1, wherein said suture anchor consists of a tubular member and said suture eyelet, said tubular member defining both said receiver and said coil member.

13. An endoscopic deployment system according to claim wherein said suture anchor coil member is tapered.

14. An endoscopic deployment system according to claim wherein said suture anchor coil member has a variable pitch.

15. An endoscopic deployment system for placing a suture anchor at a site within a mammal comprising:

an elongated flexible delivery member having proximal, intermediate, and distal regions, proximal and distal ends, an elongate shaft member having proximal and distal ends, a handle coupled to said proximal end of said shaft member, wherein rotation of said proximal end of said shaft member causes the distal end of said shaft member to rotate;

a coupling assembly fixedly coupled to the distal region of said delivery member including an engagement post;

a suture anchor having proximal and distal ends, a tubular receiver having a central longitudinal axis, a coil member positioned at said distal end of said suture anchor, and a suture eyelet rotatable relative to said receiver; and a sheath having proximal and distal ends, the sheath extending over said shaft member of said delivery member such that the distal end of said sheath is located proximal to said suture anchor;

wherein:

said delivery member is operable between a first operable configuration and a second operable configuration;

when said delivery member is in said first operable configuration, said suture anchor is releasably coupled to said coupling assembly whereby said engagement post couples with said receiver and rotation of the distal end of said shaft member results in rotation of said suture anchor such that when said suture anchor is in contact with tissue, rotation of the distal end of said shaft member causes said coil member of said suture anchor to engage the tissue; and when said delivery member is in said second operable configuration, said sheath is advanced distally over said shaft member so as to dislodge said suture anchor from said engagement post.

16. An endoscopic deployment system according to claim 15, wherein said handle is operable to rotate the proximal end of said shaft member, which results in rotation of the distal end of said shaft member.

17. An endoscopic deployment system according to claim 15, further comprising a suture anchor release surface located proximal to said suture anchor, said handle actuatable to move said suture anchor release surface distal into contact against the proximal surface of said suture anchor to disengage said suture anchor from said engagement post.

18. An endoscopic deployment system according to claim 17, wherein said handle is actuated to move said suture anchor release surface by operating a spring-release or helically advancing a coupler to which said suture anchor release surface is coupled.

19. An endoscopic deployment system according to claim 15, wherein said flexible delivery member is sufficiently flexible to be positioned through a tortuous path.

20. An endoscopic deployment system according to claim 15, wherein said elongate sheath is decoupled from said handle.

21. An endoscopic deployment system according to claim 15, wherein the distal region of said delivery member includes a first rotation key, and said suture anchor includes a second rotation key, wherein said first and second rotation keys rotationally interfere with each other.

22. An endoscopic deployment system according to claim 15, wherein said engagement post includes one of a recess and tab, and said suture anchor includes the other of a recess and a tab, and when said engagement post is coupled with said receiver, said tab and said recess rotationally interfere such that axial rotation of said engagement post results in rotation of said suture anchor.

23. An endoscopic deployment system for placing a suture anchor at a site within a mammal comprising:

an elongated flexible delivery member having proximal, intermediate, and distal regions, proximal and distal ends, an elongate shaft member having proximal and distal ends, a handle coupled to said proximal end of the shaft member, wherein rotation of said proximal end of said shaft member causes the distal end of said shaft member to rotate;

a coupling assembly fixedly coupled to the distal region of said delivery member including an engagement post;

a suture anchor having proximal and distal ends, a tubular receiver having a central longitudinal axis, a coil member positioned at said distal end of said suture anchor, and a suture eyelet rotatable relative to said receiver; and a suture anchor release surface located proximal to said suture anchor, said handle actuatable to move said suture anchor release surface distal into contact against the proximal surface of said suture anchor to disengage said suture anchor from said engagement post, said handle actuated to move said suture anchor release surface by operating a spring-release or helically advancing a coupler to which said suture anchor release surface is coupled;

wherein:

said delivery member is operable between a first operable configuration and a second operable configuration;

when said delivery member is in said first operable configuration, said suture anchor is releasably coupled to said coupling assembly whereby said engagement post couples with said receiver and rotation of the distal end of said shaft member results in rotation of said suture anchor such that when said suture anchor is in contact with tissue, rotation of the distal end of said shaft member causes the coil member of said suture anchor to engage the tissue; and when said delivery member is in said second operable configuration, said suture anchor is detached from said coupling assembly.

24. An endoscopic deployment system according to claim 23, wherein said handle is operable to rotate the proximal end of said shaft member, which results in rotation of the distal end of said shaft member.

25. An endoscopic deployment system according to claim 23, wherein said elongate sheath is decoupled from said handle.

26. An endoscopic deployment system for placing a suture anchor at a site within a mammal comprising:

an elongated flexible delivery member having proximal, intermediate and distal regions, proximal and distal ends, an elongate shaft member having proximal and distal ends, a handle coupled to said proximal end of said shaft member, the distal region of said delivery member including a first rotation key, wherein rotation of said proximal end of the shaft member causes the distal end of said shaft member to rotate;

a coupling assembly fixedly coupled to the distal region of said delivery member including an engagement post; and a suture anchor having proximal and distal ends, a tubular receiver having a central longitudinal axis, a coil member positioned at said distal end of said suture anchor, a suture eyelet rotatable relative to said receiver, and a second rotation key, wherein said first and second rotation keys rotationally interfere with each other; and wherein:

said delivery member is operable between a first operable configuration and a second operable configuration;

when said delivery member is in said first operable configuration, said suture anchor is releasably coupled to said coupling assembly whereby said engagement post couples with said receiver and rotation of the distal end of said shaft member results in rotation of said suture anchor such that when said suture anchor is in contact with tissue, rotation of the distal end of said shaft member causes said coil member of said suture anchor to engage the tissue; and when said delivery member is in said second operable configuration said suture anchor is detached from said coupling assembly.

27. An endoscopic deployment system according to claim 26, wherein said handle is operable to rotate the proximal end of said shaft member, which results in rotation of the distal end of said shaft member.

28. An endoscopic deployment system according to claim 26, further comprising a suture anchor release surface located proximal to said suture anchor, said handle actuatable to move said suture anchor release surface distal into contact against the proximal surface of said suture anchor to disengage said suture anchor from said engagement post.

29. An endoscopic deployment system according to claim 26, wherein said flexible delivery member is sufficiently flexible to be positioned through a tortuous path.

30. An endoscopic deployment system according to claim 26, wherein said elongate sheath is decoupled from said handle.

31. An endoscopic deployment system according to claim 26, wherein said engagement post includes one of a recess and tab, and said suture anchor includes the other of a recess and a tab, and when said engagement post is coupled with said receiver, said tab and said recess rotationally interfere such that axial rotation of said engagement post results in rotation of said suture anchor.

32. An endoscopic deployment system for placing a suture anchor at a site within a mammal comprising:

an elongated flexible delivery member having proximal, intermediate and distal regions, proximal and distal ends, an elongate shaft member having proximal and distal ends, a handle coupled to said proximal end of said shaft member, wherein rotation of said proximal end of said shaft member causes the distal end of said shaft member to rotate;

a coupling assembly fixedly coupled to the distal region of said delivery member, said coupling assembly including an engagement post having at least one recess; and a suture anchor having proximal and distal ends, a tubular receiver having a central longitudinal axis, a coil member positioned at said distal end of said suture anchor, a suture eyelet rotatable relative to said receiver, and at least one tab;

wherein:

said delivery member is operable between a first operable configuration and second operable configuration;

when said delivery member is in said first operable configuration, said suture anchor is releasably coupled to said coupling assembly whereby said engagement post couples with said receiver and said at least one tab and at least one recess rotationally interfere such that axial rotation of said engagement post results in rotation of said suture anchor such that when said suture anchor is in contact with tissue, rotation of the distal end of said shaft member causes the coil member of said suture anchor to engage the tissue; and when said delivery member is in said second operable configuration, said suture anchor is detached from said coupling assembly.

33. An endoscopic deployment system according to claim 32, wherein said handle is operable to rotate the proximal end of said shaft member, which results in rotation of the distal end of said shaft member.

34. An endoscopic deployment system according to claim 32, further comprising a suture anchor release surface located proximal to said suture anchor, said handle actuatable to move said suture anchor release surface distal into contact against the proximal surface of said suture anchor to disengage said suture anchor from said engagement post.

35. An endoscopic deployment system according to claim 32, wherein said flexible delivery member is sufficiently flexible to be positioned through a tortuous path.

36. An endoscopic deployment system according to claim 32, wherein said elongate sheath is decoupled from said handle.

37. An endoscopic deployment system according to claim 32, wherein the distal region of said delivery member includes a first rotation key, and said suture anchor includes a second rotation key, wherein said first and second rotation keys rotationally interfere with each other.

38. An endoscopic deployment system according to claim 32, wherein said suture anchor consists of a tubular member defining both said receiver and said coil member.

39. An endoscopic deployment system according to claim 32, wherein said suture anchor coil member is tapered.

40. An endoscopic deployment system according to claim 32, wherein said suture anchor coil member has a variable pitch.

* * * * *